United States Patent

Gorenstein et al.

[19]

[11] Patent Number: 6,064,945
[45] Date of Patent: May 16, 2000

US006064945A

[54] SYSTEM AND METHOD FOR DETERMINING MOLECULAR WEIGHT AND INTRINSIC VISCOSITY OF A POLYMERIC DISTRIBUTION USING GEL PERMEATION CHROMATOGRAPHY

[75] Inventors: Marc V. Gorenstein, Needham; Yefim Brun, Hopkinton, both of Mass.

[73] Assignee: Waters Investments Limited, New Castle, Del.

[21] Appl. No.: 09/027,443

[22] Filed: Feb. 20, 1998

[51] Int. Cl.[7] .................................................... G01N 31/60
[52] U.S. Cl. ................................................ 702/23; 702/30
[58] Field of Search ................................ 702/27, 30, 23; 73/61.52; 210/656

[56] References Cited

U.S. PATENT DOCUMENTS 4,775,943  10/1988  Chamberlin et al. .................... 364/497

OTHER PUBLICATIONS

Jackson and Barth, Handbook of Size Exclusion Chromatography, Chromatographic Science Series, vol. 69, pp. 103–145, Unknown month, 1995.

P. Tackx and F. Bosscher, Analytical Communications, Oct. 97, vol. 34 (295–297) Systematic Deviations due to Random Noise Levels in Size Exclusion Chromatography Coupled With Multi Angle Laser Light Scattering.

David W. Short, Journal of Liquid Chromatography, 16(16), 3371–3391 (1993) Differential Molecular Weight Distributions In High Performance Size Exclusion Chromatography.

S. Podzimek, Journal of Chromatography A, 677 (1992) 21–24, Characterization of synthetic resins by gel permeation chromatography with a multi–angle laser light scattering detector.

R. Lew, P. Cheung, S.T. Balke, and T. H. Mourey, Journal of Applied Polymer Science, vol. 47, 1685–1700 (1993) SEC—Viscomter Detector Systems. I. Calibration and Determination of Mark–Houwink Constants.

James Lesec and Gisele Volet, Journal of Liquid Chromatography, 13(5), 831–849 (1990). Data Treatment In Aqueous GPC With On–Line Viscometer and Light Scattering Detectors.

James Lesec and Gisele Volet, Journal of Applied Polymer Science: Applied Polymer Symposium 45, 177–189 (1990), Data Treatment In Multidetetion Gel Permeation Chromatography.

Cheng–Yih Kuo, Theodore Provide, M.E. Koehler, A.F. Kah, American Chemical Society 1987, 0097–61556/87/0352–0130, Use of a Viscometric Detector for Size Exclusion Chromatography Characterization of Molecular Weight Distribution and Branching in Polymers.

Christian Jackson and Howeard G. Barth, Handbook of Size Exclusion Chromatography, vol. 69, Chromatographic Science Series, Molecular Weight Sensitive Detectors For Size Exclusion Chromatography (pp. 103–145).

W.W. Yau, S.D. Abbott, G.A. Smith, and M.Y. Keating, 1987 American Chemical Society, Chapter 5, 0097–6156/87/0352, pp. 81–103, A New Stand–Alone Capillary Viscometer Used as a Contuous Size Exclusion Chromatographic Detector.

*Primary Examiner*—Timothy P. Callahan
*Assistant Examiner*—Linh Nguyen
*Attorney, Agent, or Firm*—Brian Michaelis; Anthony J. Janiuk

[57] ABSTRACT

A system and method for analyzing data from a gel permeation chromatography (GPC) or size exclusion chromatography (SEC) system for determining a polymeric sample's molecular weight distribution (MWD) and intrinsic viscosity law (IVL). Data from two or more detectors is used with a least-squares minimization fit. A novel method includes the simultaneous determination of a sample's MWD and IVL using data from two or more detectors. Detectors include a Light Scattering (LS) detector, viscometer (V) and a refractive index (RI) detector. The present invention is insensitive to detector noise in the baseline regions of the peak curve.

18 Claims, 16 Drawing Sheets

SYSTEM AND METHOD FOR DETERMINING MOLECULAR WEIGHT AND INTRINSIC VISCOSITY OF A POLYMERIC DISTRIBUTION USING GEL PERMEATION CHROMATOGRAPHY

FIELD OF THE INVENTION

The present invention relates to analysis of data from gel permeation chromatography (GPC) instrumentation, and more particularly to a computer system and method for analyzing data to determine absolute molecular weight and intrinsic viscosity.

BACKGROUND OF THE INVENTION

The molecular structure of a synthetic polymer determines its end-use and its process characteristics, such as hardness, tensile strength, drawability, elastic modulus, and melt viscosity. The most important determinants that define the molecular structure of synthetic polymers are the chemical nature of their repeating units, their molecular weight distribution (MWD), and their molecular topology (branching).

The separation of a polymer sample by gel permeation chromatography (GPC) followed by detection allows one to determine the molecular weight distribution (MWD) and the intrinsic viscosity law (IVL) of a polymeric sample. The IVL can reveal the branching properties of a sample. Another term used for GPC is size exclusion chromatography (SEC).

In a GPC separation, a molecule's effective size, not its molecular weight per se, determines its elution volume. For example, two polymers may have the same molecular weight, but may differ in composition or branch topology. Such differences can lead to different elution volumes. Thus, elution volume by itself determines a sample's molecular weight distribution in a relative, not an absolute sense.

Following separation, one or more detectors record the physical properties of the eluent stream. It is the mathematical analysis of these data from which the MWD and IVL of the sample can be obtained.

When narrow standards of known molecular weight (MW), the sum of atomic weights of all atoms in a molecule, are available, and these standards are of the same polymeric material as the sample, molecular weight calibration is straightforward to perform. Injections of the narrow standards determine the chromatography column set's MW calibration curve (log MW versus elution volume). Under these circumstances, only a single concentration detector (such as a refractive index (RI) detector) is needed to determine the MWD.

If no such standards are available, dual detection schemes can be employed to determine the sample's MWD. A first typical dual detection system employs refractive index (RI) and light scattering (LS) detection. A second known system employs RI and viscometric (V) detection. The data from both such systems can be used to determine a sample's MWD.

The RI-V detection system allows the additional determination of the molecular topology of the polymer through a plot of its intrinsic viscosity law (IVL). The IVL of a sample is its intrinsic viscosity as a function of its molecular weight. The intrinsic viscosity is the ratio of the sample's specific viscosity (measured by the viscometer) to its concentration (measured by the concentration detector).

In the case of RI-V detection, polymer calibration standards are needed to determine the MWD and IVL, but the repeat units do not need to have the same chemical nature as those of the polymer sample. The RI-LS detection strategy requires no additional calibration standards.

For both systems, the RI detector is used to measure a peak's concentration profile. In place of an RI detector, a suitably calibrated UV/V is absorbance detector, evaporative light scattering detector (EVS), or infrared (IR) detector may be substituted to perform the same function.

The LS and V detectors are commonly referred to as "molecular-weight sensitive" detectors. Such detectors respond to the product of the sample's concentration and its molecular weight raised to some power.

A combination of a concentration detector and a molecular-weight-sensitive detector greatly increases the information content available from a typical analysis. But the increase in the available information expands the complexity of data analysis. For both systems, algorithmic methods are required to analyze the detector responses in order to obtain the sample's MWD. In the RI-V system, an additional algorithmic method is needed to determine the sample's IVL.

The accuracy and the precision of the MWD and the IVL depend not only on the quality of the data obtained from the respective chromatographic systems, but also on the details of the data analysis methodology. Thus, data analysis methods become an essential element in the GPC analysis of polymers.

At evenly spaced time intervals, each detector records a measurement of the properties of the separated sample as it elutes from the column and passes through a detector's flow cell. Each measurement, averaged over a narrow time range, corresponds to a narrow range in the sample's molecular weight distribution. The molecular weight range corresponding to a measurement recorded at a single time interval is referred to as a "slice".

A slice can be referenced by its slice number, its elution time, or its elution volume. Typically, elution volume is obtained by multiplying the elution time of a slice by the nominal flow rate of the pump. A particular slice is typically referred to by its slice number or elution volume, with no loss of generality.

The RI, LS, and V detectors are used to measure, respectively, the concentration $c_i$, the Rayleigh ratio $R_i$, and the specific viscosity $\eta_{sp,i}$, for each slice $i$.

If a pair of chromatographic profiles are obtained from two detectors, the ratio of the respective responses can be formed to obtain useful quantities. For example, if $c_i$ and $R_i$ are the measurements of concentration and the Rayleigh ratio from the ith slice, the ratio $\rho_i = R_i/c_i$ is proportional to the molecular weight of that slice. If $c_i$ and $\eta_{sp,i}$ are the slice measurements of concentration and specific viscosity, the ratio $[\eta]_i = \eta_{sp,i}/c_i$ equals the intrinsic viscosity of the slice.

Both the MWD and IVL need to be measured over the whole peak region. Typically, this is accomplished by fitting a smooth parameterized model to these ratios as a function of slice number or elution volume. The logarithm of the ratios, $\log(R_i/c_i)$ and $\log(\eta_{sp,i}/c_i)$, both tend to be nearly linear functions of elution volume, so low-order polynomials as a function of elution volume are typically fit to these quantities.

A major problem is that the noise present in the detector responses introduces errors in the quantities computed from slice measurements. Each of the known detectors employed for GPC contains non-idealities in their responses. Typically, these non-idealities fall into two categories, baseline drift and stochastic detector noise. Detector noise can also be referred to as system noise. Baseline drift in a thermally stabilized chromatograph is accurately compensated for by baseline correction procedures.

Detector noise is an irreducible component of the measurement process. The origin of this noise, seen as fluctuations in the baseline, is the result of several fundamental phenomena. One is the shot noise of the light sources such as in RI and LS detectors. Other origins are thermal noises associated with amplifiers in all detectors; fluctuations in the pump flow rate; and thermal variations. Particulate, contaminants, and bubbles can also add additional noise components to the signal.

The net result of these effects is manifested in stochastic noise added to each slice measurement. Such additive noise has zero mean and a well-defined standard deviation. The standard deviation of the noise will in general be different for the different detectors, but each detector's noise is constant throughout the separation.

The effect of the detector-noise-induced error in the slice-measurements is to introduce error in the quantities $\log(R_i/c_i)$ and $\log(\eta sp,i/c_i)$. Because $c_i$ is in the denominator, the noise in these quantities increases as the response in the concentration profile decreases. Because of the logarithm, the noise in these quantities also increases as the response of the molecular-weight-sensitive detector decreases. Thus, the noise in $\log(R_i/c_i)$ and $\log(\eta sp,i/c_i)$ increases dramatically in the tails (leading and trailing edges) of a chromatographic peak.

Further, near the peak tails, the noise in the responses can cause the ratios to have negative values. The logarithm of a negative number is not defined. Eliminating such slice data will bias the results. This issue of dealing with the logarithm of the response ratios is well described in the recent paper "Systematic Deviations due to Random Noise Levels in Size Exclusion Chromatography Coupled With Multi Angle Laser Light Scattering" by P. Tackx and F. Fosscher, 1997, *Anal. Comm.* 34, 295–297.

The question remains as to how to fit a smooth model curve to $\log(R_i/c_i)$ and $\log(\eta sp,i/c_i)$ across a complete peak profile given the presence of detector noise.

Prior to the present invention, it was assumed that in the peak tails, the quantities $\log(R_i/c_i)$ and $\log(\eta sp,i/c_i)$, because they appeared dominated by noise, contained no useful information. Least-squares fitting of models were then confined to the "heart" of the peaks where the ratios' signal-to-noise ratio (SNR) were high. Users were required to manually decide the demarcation between the region to which the model is fit, and regions to exclude from the model fit.

However, to determine the MWD and IVL throughout the peak, the values of these quantities were nevertheless needed in the peak tails. The prior practice was to extrapolate the model results to the peak tails. The results obtained from such extrapolations are notoriously sensitive to the choice of the fitting region and the extrapolation method, as Tackx and Fosscher point out.

SUMMARY OF THE INVENTION

The present invention provides an accurate data analysis method that can be applied to the data acquired from detectors for determining a polymeric sample's molecular weight distribution (MWD) and intrinsic viscosity law (IVL).

According to the invention, a pair of chromatographic profiles is obtained from two detectors, and one set of responses is compared to a model that is a function of another set of responses. For example, if $c_i$ and $R_i$ are the measurements of concentration and the Rayleigh ratio for the ith slice, the quantity $R_i$ is compared to a model of $R_i$ obtained from $c_i$. If $c_i$ and $\eta sp,i$ are the measurements of concentration and the specific viscosity from the ith slice, the quantity $\eta sp,i$ is compared to a model of $\eta sp,i$ obtained from $c_i$. This method then eliminates the need to take the ratio of profiles and the logarithm of these ratios and thereby allows the use of slice measurements made throughout a peak profile, including the regions in the peak tails.

In a first embodiment of the invention, an accurate method for determination of MWD and IV of polymeric samples using the technique of GPC or SEC separations and two or more detectors is provided.

A first implementation of the first embodiment of the present invention includes a method of using least-squares minimization that takes a first detector signal, constructs an initial model curve using a parameterized model curve which describes sample properties. Least-squares minimization is then performed on the initial model curve and a second detector signal to produce a best fit model curve and parameters.

A second implementation of the first embodiment includes a method for determining a sample's molecular weight calibration curve using two or more detectors. Data from a concentration detector is processed into slices, and an initial model curve using a parameterized model curve describing log M (log molecular weight) versus elution volume is generated. This initial model curve is used to describe the Rayleigh ratio of the slices from the concentration detector. Second data from a Light Scattering (LS) detector is processed into the Rayleigh ratios of the slices. Least-squares minimization is then performed on the initial model curve and the Rayleigh ratios of the slices from the second detector data, resulting in a best fit model curve and parameters. The sample's molecular weight distribution (MWD) is then calculated.

A third implementation of the first embodiment of the present invention includes a method for determining a sample's intrinsic viscosity versus elution volume using two or more detectors. Data from a concentration detector is processed into slices, and an initial model curve using a parameterized model curve describing $\log [\eta_i]$ versus elution volume is generated. This initial model curve describes the specific viscosity of the slices from the concentration detector. Second data from a viscometer (V) detector is processed into the specific viscosities of the slices. Least-squares minimization is then performed on the initial model curve and specific viscosity of slices from the second detector data, resulting in a best fit model curve describing $\log [\eta_i]$ versus elution volume.

In a second embodiment of the present invention, the simultaneous determination of a sample's MWD and IVL using data from two or more detectors is performed. Data from a concentration detector is processed into slices. An initial model curve is constructed using this data, using a parameterized model curve describing $\log [\eta_i]$ versus log M for the sample, and using the hydrodynamic volume of slices from a universal calibration curve. This initial model curve describes the specific viscosity of the slices as a function of the concentration detector responses. Second data from a viscometer (V) detector is processed into the specific viscosities of the respective slices. Least-squares minimization is then performed on the initial model curve, and specific viscosity of respective slices from the second detector data, resulting in a best fit model curve describing log $[\eta_i]$ versus log M. From this best fit model curve, the IVL and MWD are determined.

A third embodiment of the present invention includes a reformulation of a least squares minimization fit to eliminate the use of ratios and logarithms, thereby allowing the fit to include all the data throughout a peak.

A fourth embodiment of the present invention includes using weighted least-squares minimization fit where noise in compared quantities varies throughout the whole of the peak region, whereby the least-squares fit then can be carried out over the whole of the peak region.

An advantage of the present invention is that it allows the inclusion of regions that contain no signal; e.g., baseline responses that fluctuate about zero from either, or both, detectors. Another advantage of the present invention is the improved accuracy and precision of the sample's MWD, as determined by the two systems under consideration. Further, the least-squares problem is formulated to avoid taking ratios or logarithms of ratios of noisy data. Also, the present invention is considerably less sensitive to measurement errors, especially in the tails of the peaks. The present invention provides improved accuracy and precision of the IVL for the second embodiment.

Still another advantage of the present invention is that the IV law and molecular weight calibration are estimated from a single fit to all the slice data. The need to perform multiple fits and extrapolations is avoided, as are systematic errors that result from performing additional fits.

BRIEF DESCRIPTION OF THE DRAWING

The foregoing and other features and advantages of the present invention will be more fully understood from the following detailed description of illustrative embodiments, taken in conjunction with the accompanying drawings in which.

DETAILED DESCRIPTION

Figure 1:
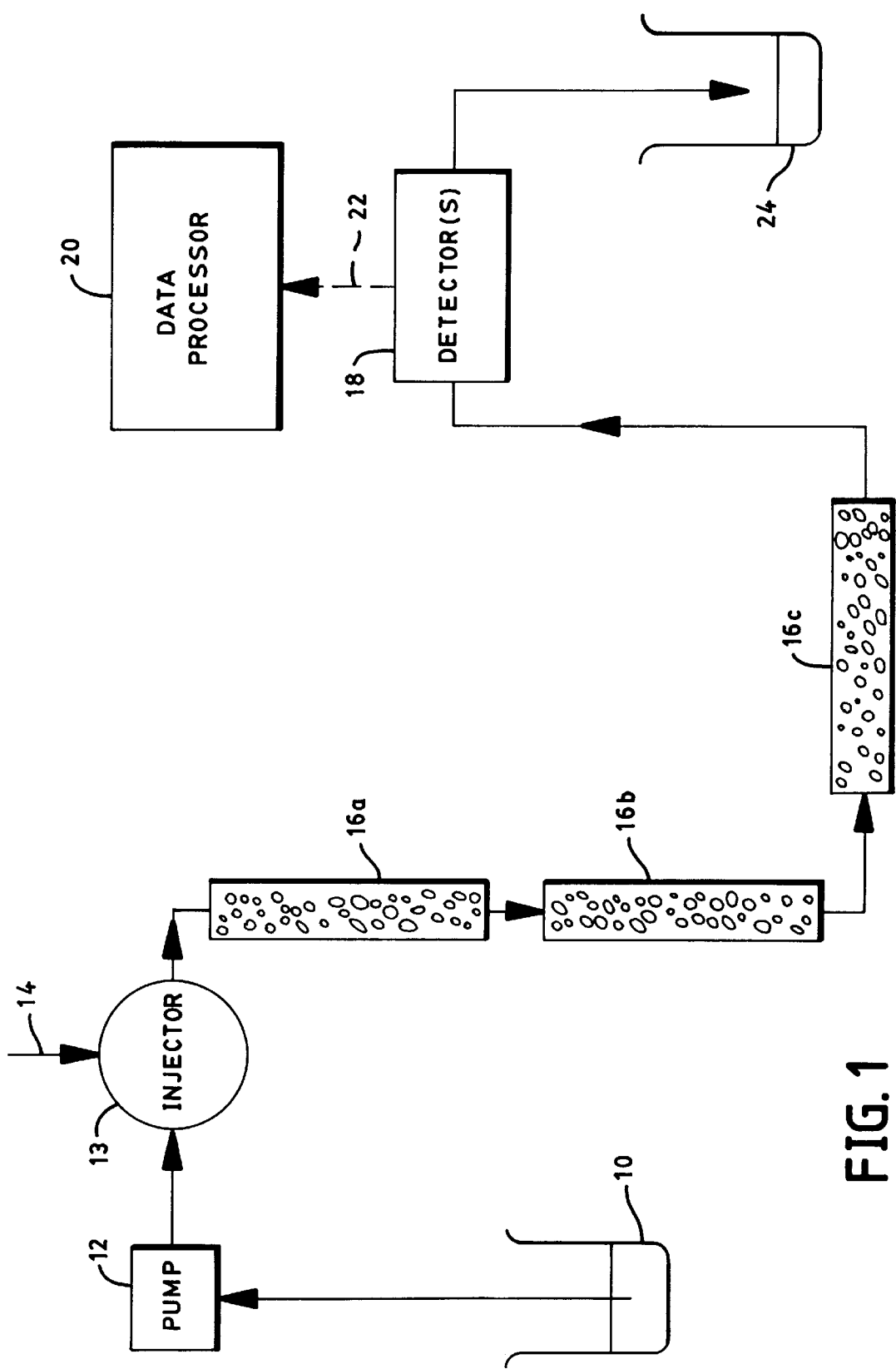
FIG. 1 is an overview of a Gel Permeation Chromatography system which provides data to be analyzed by a system including the present invention.

An illustrative gel permeation chromatography (GPC) system for analyzing molecular weight distributions according to the present invention is illustrated in FIG. 1. A solvent reservoir 10 provides solvent which is pumped by a solvent pump 12. At the injection valve 13, the polymeric sample 14 is introduced into the solvent flow. The solvent along with the polymeric sample 14 then passes through a set of columns 16 which contain the chromatographic bed. The solvent then passes through a detector 18, where one or several detectors analyze the solution and determine the presence and properties of polymer chains. This information is supplied to a data processor 20, as shown by arrow 22. The waste solution then collects in a container 24.

The GPC columns 16 contain packed beads (the chromatographic bed) that possess a distribution of pore sizes. An illustrative embodiment of such a system is a Waters 150CV+GPC Viscometry Chromatography System, and Styragel Columns, both manufactured by Waters Corporation, 34 Maple Street Milford, Mass., 01757.

Injection of the sample 14 into the flowing stream forces it through the column set 16. The separation is effected by a sieving mechanism. The pores exclude the larger molecules and retain the smaller molecules. Larger molecules see a column set having a relatively small effective volume. Smaller molecules see a column set having a relatively large effective volume. Consequently, the larger molecules elute first, and the smaller molecules elute later. The detectors 18 follow the column set 16 and measure the physical properties of the eluent.

Figure 2:
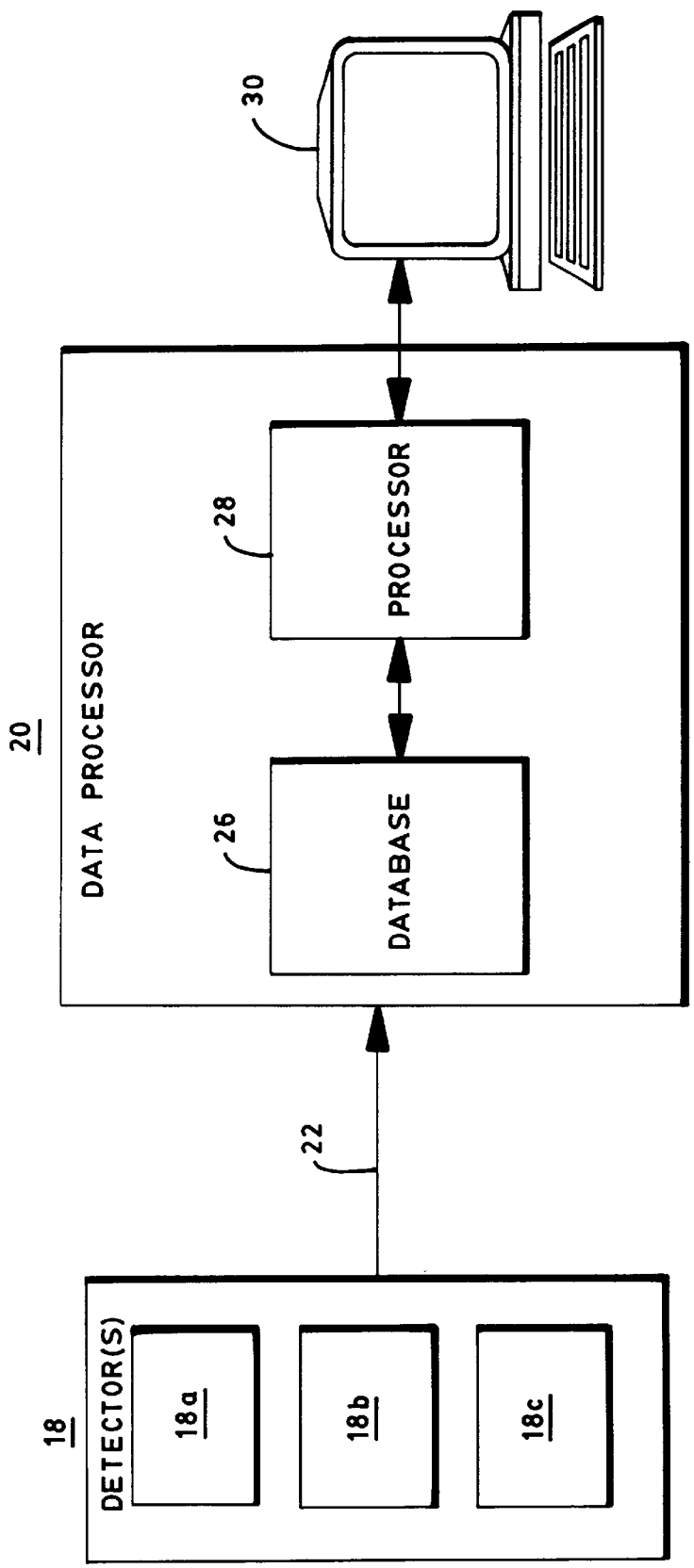
FIG. 2 is an illustrative computer system for analyzing data according to the present invention.

The data processor 20 FIG. 2 includes a database 26 and a processor 28. The database 26 includes long-term storage such as magnetic disks, tapes and opto-magnetic discs. The database 26 in this illustrative embodiment is a relational database. The processor 28 accesses the data stored in database 26 for processing and producing information which may be stored back in the database 26, or displayed on a workstation 30, or printed out (not shown). The data processor 20 can also include instrumentation to process and convert the data 22, including A/D (analog to digital) conversion circuits, sample and holds, and other devices (not shown).

In the illustrative embodiment, the data processor is a general purpose computer, such as an Intel Pentium® based personal computer running Microsoft Windows® 95 or Windows NT. The processing application software is Millennium$^{32}$® as produced by Waters Corporation of Milford, Mass. Millennium$^{32}$ is a chromatography information and systems manager that allows a chromatographer to control instrumentation, and to acquire, store and retrieve data obtained from detectors. It also allows the chromatographer to process that data and store, retrieve display, and print the processed results in graphical and tabular form.

The Millennium[32] software product includes several components. One software component controls instrumentation (the pump 12, the autoinjector 13, and the detectors 18) and acquires data (primarily from the detectors). Another component is the database 26 which is an Oracle database that stores and serves up information.

Another component is the application software that processes and extracts information from the data and presents it in reports. A report generator allows the user to create, manage and print reports. A graphical user interface (GUI) allows the user to interact with all these subsystems and components from the monitor 30. The illustrative embodiment of the present invention is implemented within the data processing component of Millennium[32].

Two categories of detectors can provide signal inputs 22 to Millennium[32]. One category comprises detectors manufactured by Waters, the other contains third party detectors. The output from Water's detectors communicate via an IEEE-488 interface (IEEE-488 is the IEEE Standard Digital Interface for Programmable Instrumentation, ANSI/IEEE Standard 488-1978). The signal from the detector is in analog form on the IEEE-488 cable. The IEEE-488 cable connects to Millennium[32] via a printed circuit board plugged into the ISA slot on a PC motherboard, as is known in the art. This printed circuit board is a Waters product called a BusLACE. The BusLACE digitizes the signals and communicates with the PC. The IEEE-488 interface is implemented as a daisy-chain network so multiple detector modules and instruments can plug into the one IEEE-488 connector on the BusLACE.

The output 22 from a third party detector 18 is assumed to be in analog form. The detector output signal is impressed on a pair of wires, enclosed within a shielded cable. The shielded cable connects to a piece of Waters electronics hardware called a SAT/IN (Satellite Input). The SAT/IN takes analog inputs from two devices and digitizes the analog input signal. The output of the SAT/IN is an RS-232 line, which provides an input to the BusLACE. Thus, the BusLACE accepts two entirely different types of input, the IEEE-488 signals from Waters hardware, and the RS-232 signals from third party detectors.

The detectors 18 include refractive index (RI) detectors, light scattering (LS) detectors, and viscometer (V) detectors.

The RI detector responds to the solution's refractive index. Given the output of this detector, subtracting the detector's baseline response and dividing by the refractive index increment dn/dc for the sample gives the concentration profile of the sample, ci for the ith slice.

The RI detector is used to measure a peak's concentration profile. A suitably calibrated UV/Vis absorbance detector or evaporative light scattering detector (EVS) may be substituted in place of an RI detector to perform the same function. Any detector that can serve as a concentration detector may be used in place of the RI detector, and is within the scope of the invention. An example RI detector is the detector incorporated in a Waters 150CV+GPC Viscometry Chromatography System from Waters Corporation.

The LS detector responds to the sample by scattering light. Subtracting the detector's baseline response and applying a detector calibration procedure gives the excess Rayleigh ratio due to the sample, Ri, for each slice. An example LS detector is a miniDAWN three angle laser light scattering detector from Wyatt Technology Corp. of Santa Barbara, Calif.

The viscometer (V) detector responds to the sample plus solvent's viscosity. Subtracting the detector's baseline response, and dividing by the viscosity of the baseline gives the specific viscosity of the sample, $\eta sp,i$, for each slice. An example V detetector is the detector incorporated in a Waters 150CV+GPC Viscometry Chromatography System from Waters Corporation.

The LS and V detectors are commonly referred to as "molecular-weight sensitive" detectors, in that the detector's response is in proportion to the sample's concentration multiplied by some function of the sample's molecular weight. In the case of light-scattering, the LS detector responds to the product of concentration and molecular weight. In the case of viscometric (V) detection, the viscometer responds to the concentration multiplied by the molecular weight raised to a power of $\alpha$.

Thus, for each slice, the detectors give the concentration ci, excess Rayleigh ratio Ri, and specific viscosity $\eta sp,i$ for that slice.

Figure 3:
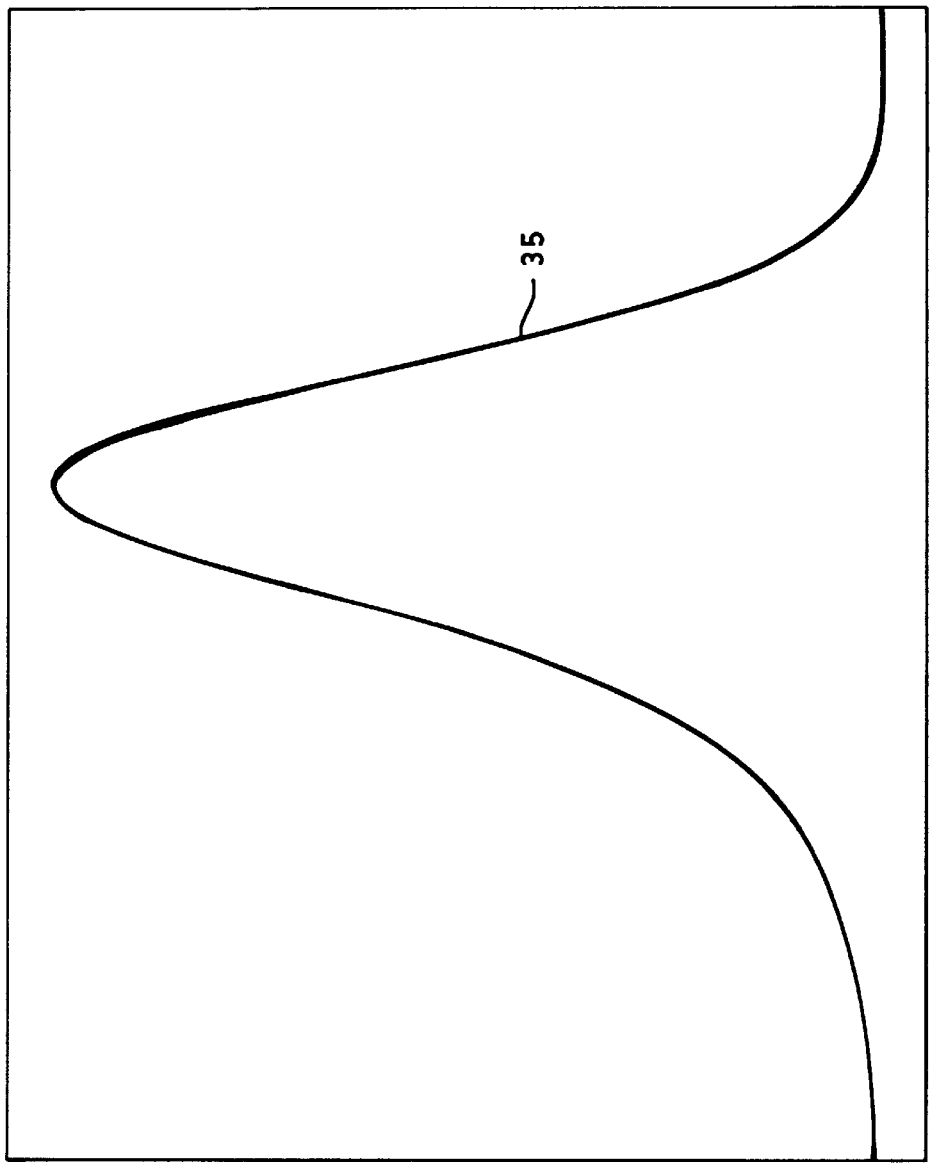
FIG. 3 is a graph of a simulated MWD of a sample, given a mass injected on column, normalized to give dm/dlogM, the mass per unit logarithmic interval of MW.

A polymeric sample 14 contains a distribution of chain lengths. This sample's MWD can be described by the relative mass (or concentration) per unit interval of molecular weight. Because of the kinetics governing the synthesis of polymers, these distributions are conventionally described by the relative mass per unit of the logarithm of MW, as illustrated in FIG. 3. The horizontal axis is log MW and the vertical axis is arbitrary. As described, a narrow, but finite, interval in log MW of the distribution is referred to as a slice.

For explanatory purposes, the simulated MWD 35 shown in FIG. 3 will be used. Given a mass injected on column, this profile is normalized to give dm/dlogM, the mass per unit logarithmic interval of MW.

Figure 5:
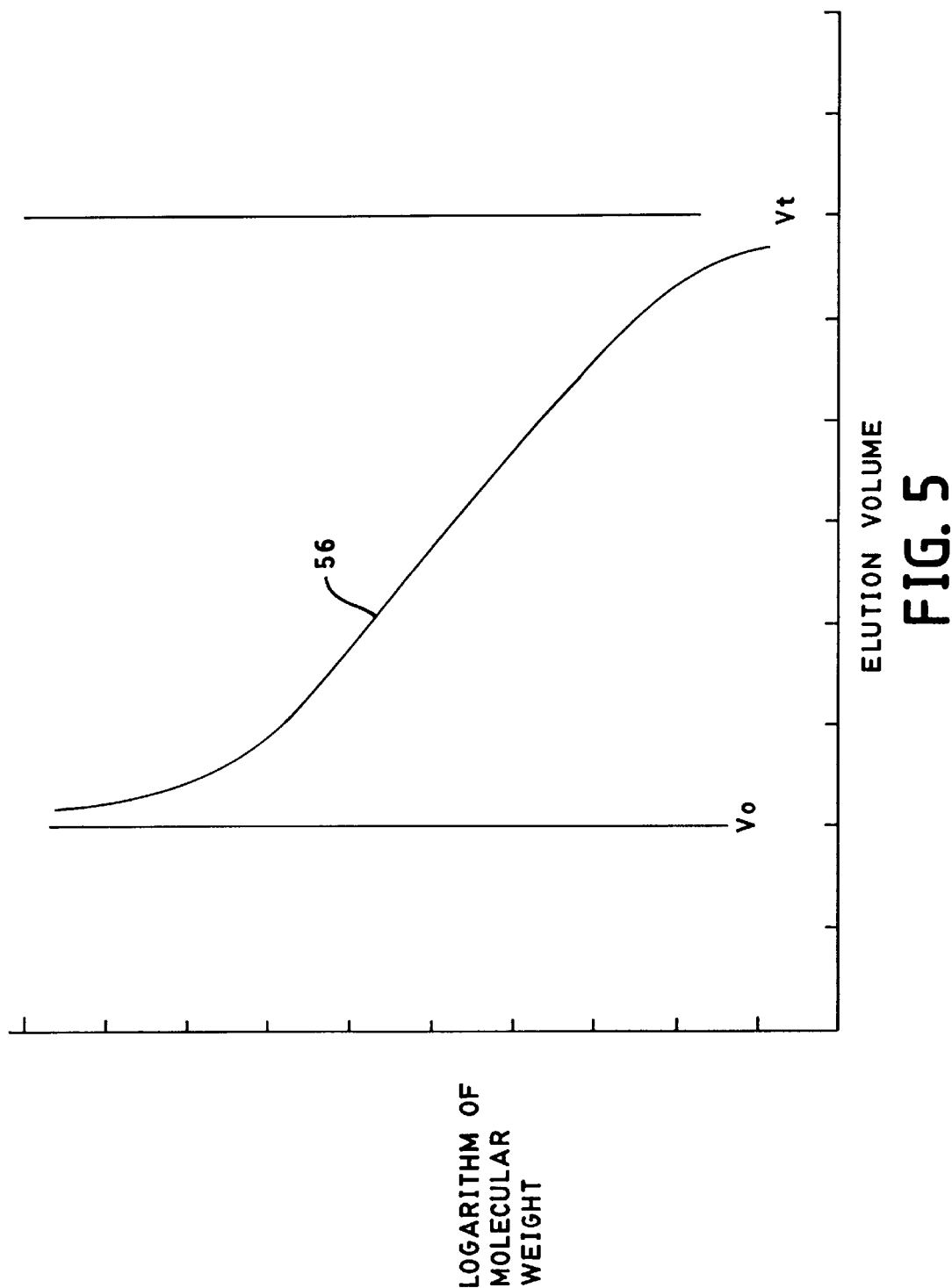
FIG. 5 is a sample molecular weight calibration curve.

FIG. 5 plots the column set's molecular weight calibration curve, which is the log of the MW versus elution volume. The x-axis in FIG. 5 is elution volume, and the y-axis is log MW. The asymptotes reflect at the high molecular weight end Vo, the total excluded volume, and at the low molecular weight end Vt, the total column volume.

This line has asymptotes at high and low MW reflecting the limits on the column set by the pore size distribution. The asymptotes reflect at the high molecular weight end Vo, the volume excluded by the beads; at the low molecular weight end the asymptote is at Vt, the total column volume. Ideally, between Vo and Vt there is an elution region where a plot of log MW versus elution volume is nearly linear. This calibration curve is sample-dependent, and it also depends upon the choice of solvent, columns, and temperature.

Figure 6:
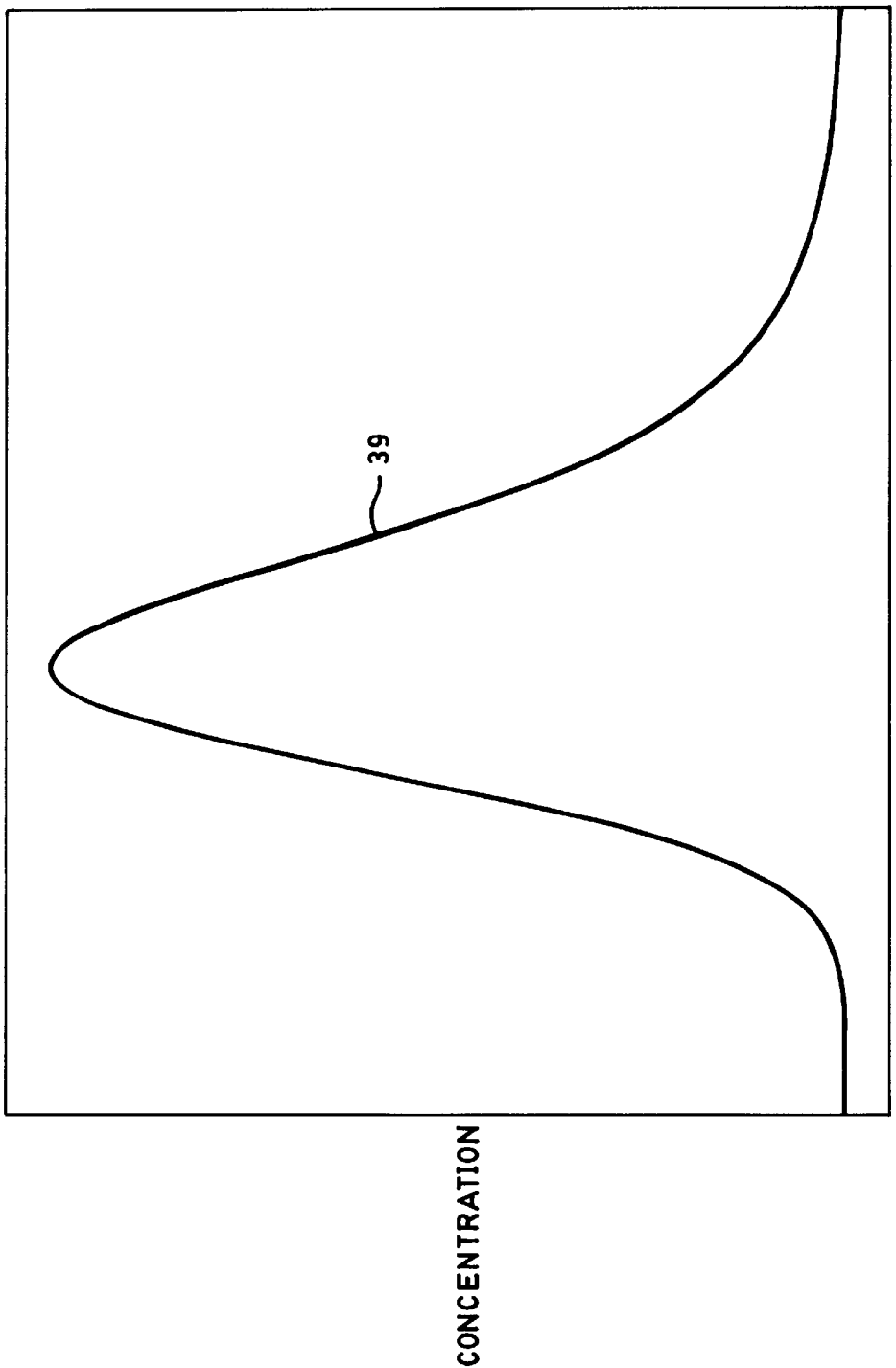
FIG. 6 is a graph showing sample concentration versus elution volume.

The column calibration of FIG. 5 applied to the MWD gives the concentration of the sample versus elution volume as it elutes from the column set 39, or c(V), plotted in FIG. 6. The x-axis is elution volume; the y-axis is concentration.

Each polymeric sample possesses a refractive index increment described by dn/dc, the change in the solution's refractive index per unit change of sample concentration. Multiplying the concentration profile by the refractive index increment, dn/dc, gives refractive index versus elution volume plot 40 in FIG. 7. This is a simulation of the RI detector response.

The excess Rayleigh ratio describes the fraction of incident light scattered by a polymer chain, when the wavelength X of the incident light is comparable to or larger than the size of the chain. Assume an incident beam of unpolarized light of intensity Io, low sample concentration c, low scattering angle $\theta$, and small particle size. Assume that the sample in a unit volume of solution scatters the light into direction θ with respect to the beam. That part of the intensity of the light that scattered by the sample I(θ) and received at distance r is given by $$\frac{I(\theta)}{I_0} = \frac{K^*(1 + \cos^2\theta)cM}{r^2} \qquad \text{Eq. (1)}$$

where K* is the optical constant expressed in terms of numerical and physical constants, as $$K^* = \frac{2\pi}{N_A}\left(n_o \frac{dn}{dc}\right)^2 \frac{1}{\lambda^4}, \qquad \text{Eq. (2)}$$

where NA is Avogadro's number, and no is the refractive index of the solvent.

The excess Rayleigh's ratio, defined to be independent of instrumental geometry, is given by $$R \equiv \frac{I(\theta)}{I_0} \frac{r^2}{(1 + \cos^2\theta)} \qquad \text{Eq. (3)}$$

Thus, at small angles, for slice i Eq. (1) becomes $$R_i = c_i M_i K^* \qquad \text{Eq.(4)}$$

so that the excess Rayleigh ratio is simply the product of the slice's concentration ci, molecular weight Mi, and the optical constant K*.

Figure 7:
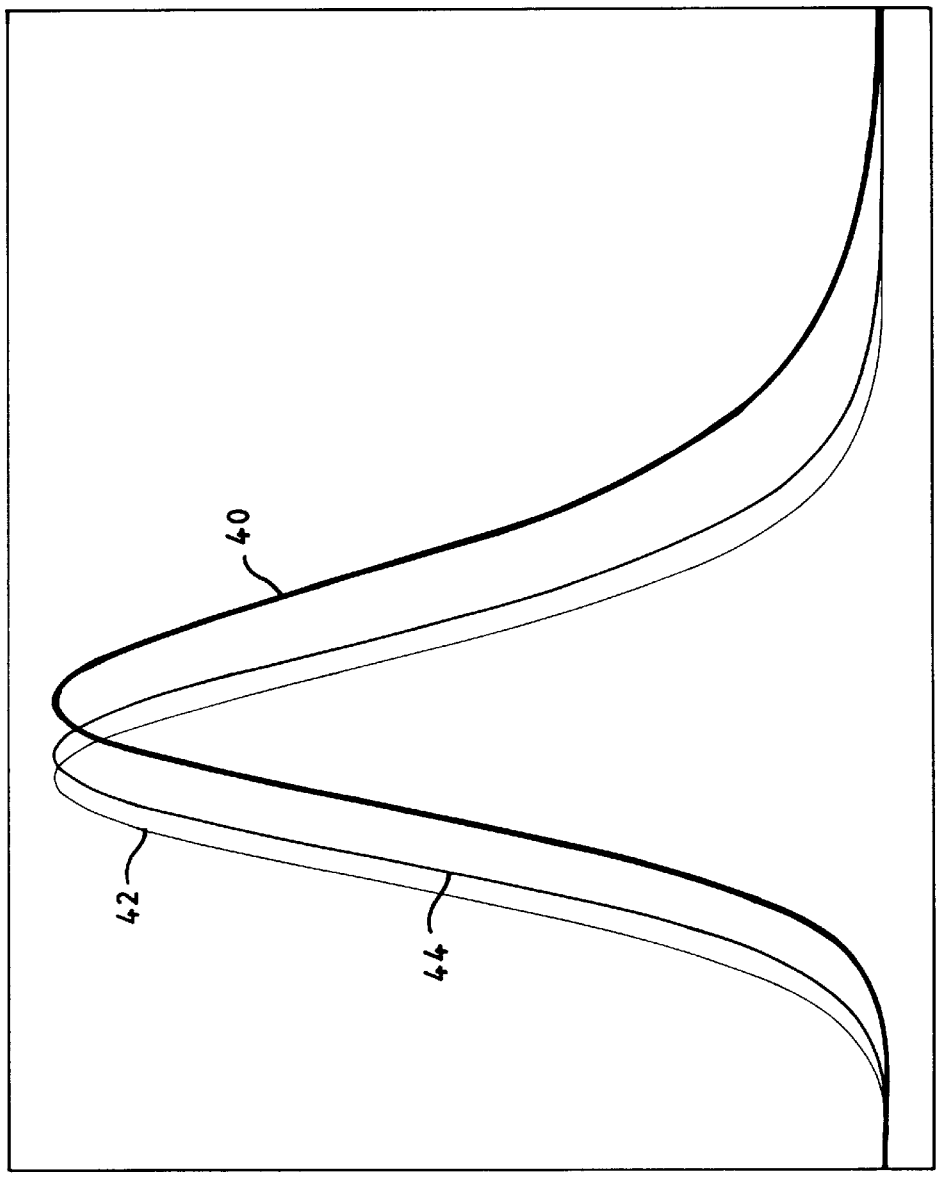
FIG. 7 illustrates the detector profiles based on the instrumental responses to the concentration profile described in FIG. 6.

The excess Rayleigh ratio versus elution volume 42 is also illustrated in FIG. 7. The Rayleigh ratio is obtained by multiplying each slice in the concentration profile in FIG. 6 by MiK*. This is the simulation of the profile measured by the LS detector.

The specific viscosity ηsp is the fractional increase in viscosity due to the presence of a sample in a viscometer. At constant flow rate, the pressure drop across a capillary tube P is proportional to the viscosity of the liquid flowing through the tube. If Po is the pressure drop due to the solvent alone, then the specific viscosity ηsp of a slice containing a polymer in solution is defined as $$\eta_{sp} \equiv \frac{P - P_0}{P_0}, \qquad \text{Eq. (5)}$$

where P is the pressure drop due to the polymer-plus-solvent solution. This expression shows that ηsp measures the increase in viscosity caused by the addition of the polymer to the solvent.

Each slice has an intrinsic viscosity [η$_i$]. The intrinsic viscosity (IV) is defined as ratio of the slice's specific viscosity ηsp divided by its concentration, c, in the limit of low concentration.

$$[\eta] = \lim_{c \to 0} \frac{\eta_{sp}}{c} \qquad \text{Eq. (6)}$$

In GPC separations, the concentrations are low enough that the intrinsic viscosity for a slice is taken to be the slice ratio as follows:

$$[\eta]_i \equiv \frac{\eta_{sp,i}}{c_i}. \qquad \text{Eq. (7)}$$

The intrinsic viscosity of a polymer varies with its molecular weight. The intrinsic viscosity law (IVL) describes the dependence of the logarithm of the sample's intrinsic viscosity on the logarithm of its molecular weight.

For unbranched polymers, the logarithm of the IV in general is proportional to the logarithm of the chain's molecular weight. The empirical Mark-Houwink intrinsic viscosity law expresses this linear relationship as $$\log[\eta_i] = \log K + \alpha \log M_i \qquad \text{Eq.(8)}$$

which is parameterized by the Mark-Houwink constants, K and α.

Polymers can be branched. Zimm and Stockmeyer developed a physical model of long-chain, branched polymers, described in Zimm, B. and Stockmeyer, W., 1949, *J. Chem. Phys.* 17, 1301–1314, which is incorporated herein by reference. Starting from this work, a model is developed describing the intrinsic viscosity for polymers with long-chain branching, which is called the Zimm-Stockmeyer (ZS) law.

In the ZS law, the distribution's intrinsic viscosity is described by four parameters, K, α, ε and λ.

The ZS law assumes that at low molecular weight the polymer is essentially unbranched. In this regime, the intrinsic viscosity law is asymptotically linear. The asymptotic slope of the intrinsic viscosity law at low molecular weight is described by the Mark-Houwink constants, K and α.

At high molecular weight, when branching dominates, the asymptotic slope of the intrinsic viscosity law is less than α, and is given by (α−ε/2), where ε is the shape factor of the polymer. Values for ε are determined by the polymer/solvent system. For example, ε is approximately 0.9 for a branched polyethylene in TCB. Values for ε range from 0.5 to 1.5.

The molecular weight at which a polymer branches is a stochastic process described by a branching probability. The value λ is defined as the branching probability per Dalton. A typical value for λ is 0.00001 per Dalton.

The ZS law intrinsic viscosity for each slice i is a function of the molecular weight of that slice, Mi, and depends on the parameters K, α, λ and ε, as follows:

$$\log[\eta]_i = \log K + \alpha \log M_i - \frac{\varepsilon}{2}\log\left[\frac{\lambda M_i}{c_1} + \sqrt{1 + \frac{\lambda M_i}{c_2}}\right] \qquad \text{Eq. (9)}$$

The ZS law is implemented to describe two possible types of branched polymers, a three-branch point and a four-branch point.

Figure 4:
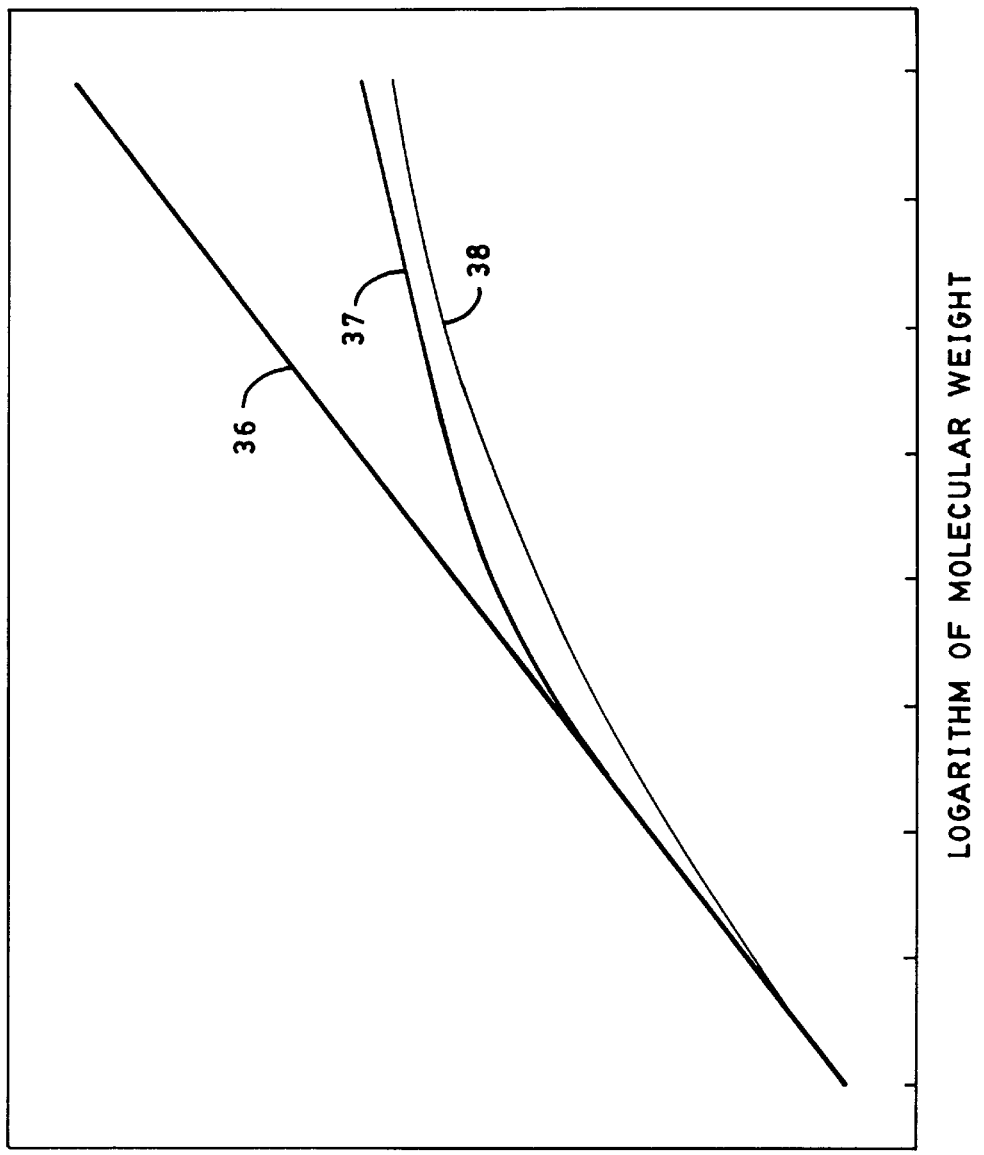
FIG. 4 is a graph showing plots of three intrinsic viscosity laws.

The coefficients for the three-branch point are c1=9π/4, and c2=7. The coefficients for the four-branch point are c1=3π/4, and c2=6. FIG. 4 illustrates the Zimm-Stockmeyer IV law. Three intrinsic viscosity laws are plotted, which are Mark-Houwink law 36, Zimm-Stockmeyer law 37, and a polynomial law 38.

The third intrinsic viscosity law (polynomial) is simply an empirical description of a sample's intrinsic viscosity based on a polynomial expansion. This "law" can be regarded as an extension of the Mark-Houwink law, so that $$\log[\eta_i] = \log K + \alpha_1 \log M_i + \alpha_2 \log^2 M_i + \ldots + \alpha_N \log^N M_i \qquad \text{Eq. (10)}$$

where N is the order of polynomial, and K and α1 are the Mark-Houwink constants.

The specific viscosity is simulated by multiplying each slice in the concentration profile in FIG. 6 by the intrinsic viscosity law (IVL) for that slice. The IV for that slice is obtained from the IVL, plotted in FIG. 4, curve 37. FIG. 7 plots this simulation of the specific viscosity versus elution volume plot 44 that would be obtained from the viscometer detector.

Figure 8:
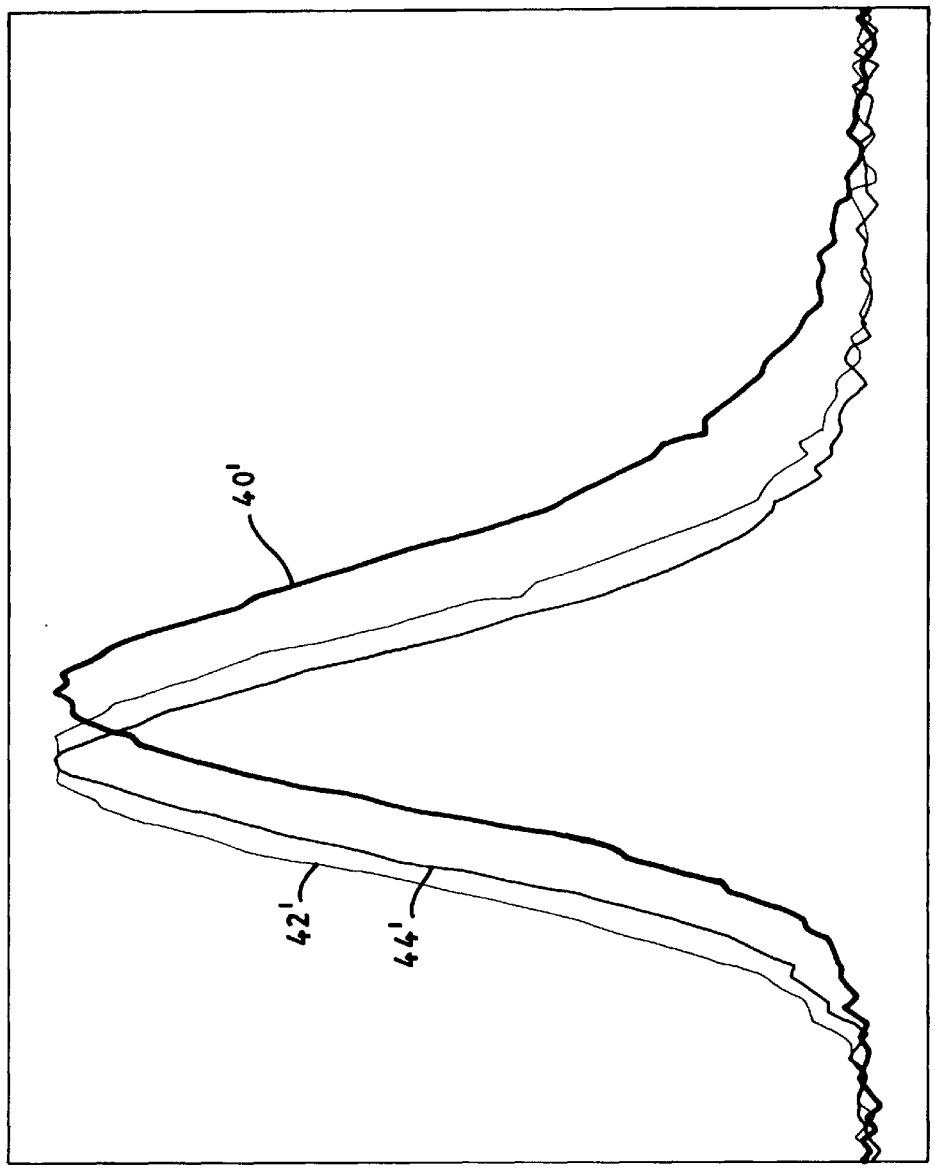
FIG. 8 illustrates the detector responses of FIG. 7 with the inclusion of detector noise.

Therefore, FIG. 7 illustrates the detector profiles based on the instrumental responses to the concentration profile described in FIG. 6. To complete the simulation, the appropriate level of detector noise must be added to each of the simulated signals. FIG. 8 illustrates the profiles after the addition of the baseline noise to each of the detector responses. Shown are the RI 40', LS 42' and V 44' detector responses. In FIG. 7 and 8 the respective profiles have been normalized to have the same peak height for clarity in plotting.

For a given chromatographic system, containing a column set and solvent, together with a given sample, retention volume is a monotonically decreasing function of a chain's molecular weight. The plot of log MW versus elution volume is termed the molecular weight calibration for the sample.

Ideally, this curve would be universal, in the sense it would apply to all samples. Unfortunately, this curve is sample dependent (as well as dependent on the solvent and column set).

There is no a priori means to determine the MW calibration curve from a given column, solvent, and sample combination. In practice, the MW calibration curve must be determined by a calibration procedure employing the collected data.

The basis of MW calibration for RI-LS detection is the relationship between the Rayleigh ratio, molecular weight, and concentration for each slice. This relationship need only be considered in the limit of scattering at zero angle and low sample concentration. In this limit, the relationship between these parameters is:

$$M_i = \frac{R_i}{c_i} \cdot \frac{1}{K^*}. \qquad \text{Eq. (11)}$$

A more general Rayleigh scattering law includes the dependence of the excess Rayleigh ratio on the scattering angle, the molecule's radius of gyration, and the second Virial coefficient. The method of the present invention applies either to this simpler or to the more complete expression.

The significance of the relationship expressed by Eq. (11) is that only the RI and LS detector responses (curves 40 and 42, or, 40' and 42') are needed to obtain a sample's molecular weight calibration curve.

If detector noise were not present, so the RI and LS profiles were free of noise as in FIG. 7, the sample's MW calibration and MWD would be straightforward to obtain. Following Eq. (11), one would, for each slice i divide 42 the LS response $R_i$ by 40 the respective RI response $c_i$. Dividing the resulting ratio by K* obtains the measurement of the molecular weight $M_i$ for that slice. The plot of log $M_i$ versus elution volume would accurately determine the samples molecular weight calibration curve, which would correspond exactly to that plotted in FIG. 5. Combined with the concentration distribution 40 described by the RI response, the exact simulated MWD shown in FIG. 3 would be recovered.

Because detector noise is always present in the RI and LS profiles, the preceding method will give results that are acceptable only in the central region of the peak. Turning to the realistic situation depicted in FIG. 8 one divides 42' the noise-affected LS response Ri by 40' the respective noise-affected RI response $c_i$, for each slice i. Each slice-ratio is divided by K* and the plot of log $M_i$ versus elution volume is plotted as 46 in FIG. 9.

Figure 9:
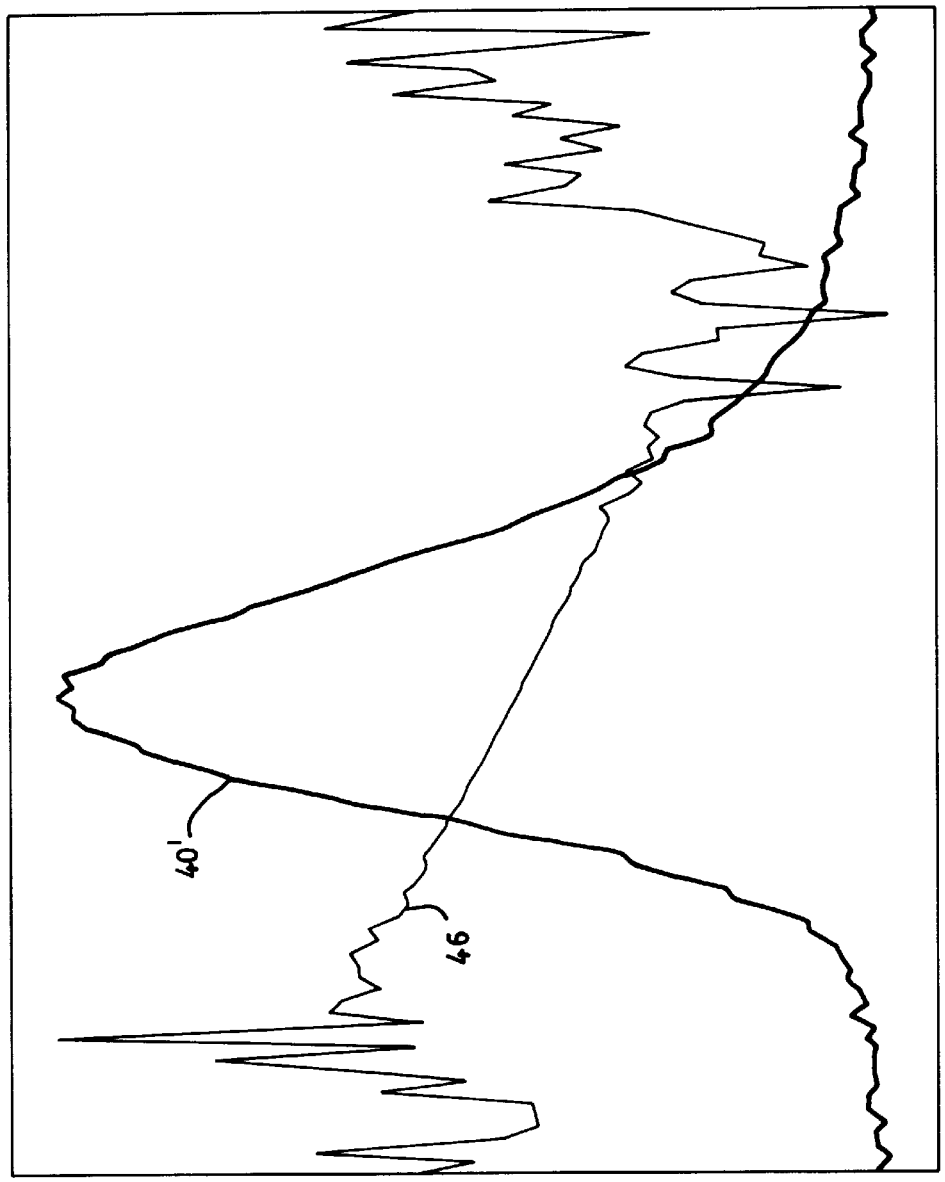
FIG. 9 illustrates the molecular weight calibration curve obtained from the slice data versus elution volume.

Thus, FIG. 9 illustrates the molecular weight calibration curve 46 obtained from the RI-LS slice data of FIG. 8 through the straightforward application of Eq. (11). Clearly, the presence of noise affects this estimate of log M, which fluctuates with high amplitude in the tail regions of the peak.

It would be an obvious mistake to use these slice-determined numbers directly as estimates of MW in the tails of the distribution. For example, the molecular weight calibration must be monotonically decreasing as elution volume increases.

In the prior art, to estimate the MWD, the strategy employed is to first form the logarithm of the ratio log $M_i$=log $(R_i/(K^*c_i))$ for each slice. The second step is to fit a low-order polynomial-curve to log $M_i$ versus elution volume. It is assumed that a fitted low-order polynomial will accurately describe to the MW calibration of the column set for this separation. Other smooth curves, other than a low-order polynomial can be employed.

In the prior art, the least-squares fitting procedure can be expressed as follows:

$$\chi^2 = \sum_{i=1}^{N} \left( \log\left(\frac{R_i}{c_i}\frac{1}{K^*}\right) - F_i(P_0, \ldots, P_M) \right)^2 \qquad \text{Eq. (12)}$$

where the left term on the right hand side is the molecular weight inferred for each slice from the combination of the RI and LS detector responses. The term on the right is the polynomial model which is used as an example, whose shape is specified by parameter values, P0, . . . ,PM, where $$F_i(P_0, \ldots, P_M) = \sum_{j=0}^{M} P_j i^j, \qquad \text{Eq. (13)}$$

and the values i are indices of the elution volume slices. The function $F_i$(P0, . . . , PM) is the logarithm of the molecular weight for slice i. Thus log $M_i$=$F_i$(P0, . . . , PM), and this relationship describes the molecular weight calibration curve as a function of slice i.

The symbol M is used in two senses herein. When referring to a slice, M or $M_i$, will stand for molecular weight. But when referring to a polynomial model curve, M will be the highest order exponent in the expansion and the model curve will be specified by M+1 adjustable parameters, $P_0, \ldots, P_M$. When referring to a general model curve, M will be the maximum number of adjustable parameters needed to specify that model curve, which will then be parameterized by $P_1, \ldots, P_M$. The symbol P, will stand for the set of parameters $P_0, \ldots, P_M$ or $P_1, \ldots, P_M$ depending on the context.

The function $F_i$(P0, . . . ,PM) is expressed as a function of the independent slice index i. One could equivalently parameterize F in terms of values that are proportional to slice index, such as elution volume or elution time.

In Equation 13, the summation is carried out over slices from i=1 to N, where N is the number of slices. The M+1 parameters P0, . . . ,PM are adjusted by a suitable optimization algorithm that finds those value of P0 , . . . ,PM that minimizes $X^{32}$. By this means, a least-squares solution that determines the model curve $$F_i = \sum_{j=0}^{M} P_j i^j$$

For RI-LS detection, this formulation of least-squares fitting has three well-known problems, all of which occur in the tails of the peaks and which are due to the presence of detector noise in the Ri and ci data. The first problem is that because of this noise, Ri or ci can fluctuate negative in the tails, so the ratio can be negative. The logarithm is undefined for negative quantities. Second, the noise induced in the term $$\log\left(\frac{R_i}{c_i} \frac{1}{K^*}\right)$$

is not symmetric about the mean value, since the logarithm is not a linear function of its argument. Third, the noise induced in $$\log\left(\frac{R_i}{c_i} \frac{1}{K^*}\right)$$

becomes large in the peak tails.

In the prior art, these limitations have been addressed by restricting the region to which the curve $$F_i = \sum_{j=0}^{M} P_j i^j$$

is fit. The fitting region is generally chosen to span the heart of the peak. The results from this fit are then extrapolated to the tails. But extrapolation of polynomial models generally gives unreliable results. In addition, it is not clear how to specify the region for the polynomial fit, and the region which is extrapolated. The results of the fit can be very sensitive to this choice of fitting region.

The method according to the invention is based on the theory of maximum likelihood, which yields optimum estimation of parameters in multi-variate models, as described in *Statistics for Phyusicists*, B. R. Martin, (1971), Academic Press, London and New York, pages 85–98. which is incorporated herein by reference.

Fitting a multi-variate curve to data containing stochastic noise is a common problem in the statistical analysis of data. The theory of maximum likelihood describes how to find parameters values that are unbiased and have minimum sensitivity to the noise in the data. Parts of the theory are applied to analysis of RI-LS and RI-V data as described below.

The stochastic noise in the RI, LS, and V detectors corresponds to the most common type of instrumental noise, which is additive, has zero mean, and is described by a Gaussian distribution parameterized by a standard deviation. For noise described by these statistics, estimation procedures based on weighted least-squares fitting are generally optimum.

In the weighted least-squares method according to the invention, the first step is to start with a set of data di where i runs from 1 to N, where N is the total number of measurements. The data is described by the model $D_i(P_1, \ldots, P_M)$, where the M parameters P describe that the model values Di. The model values Di derives from functions such as polynomial curve that can account for the data values di. Each datum di deviates from the model by noise that has a Gaussian distribution of zero mean and standard deviation σi.

The optimum (least-sensitive to noise) estimate of the parameters P is obtained by finding those parameter values that minimize the following expression for $X^2$:

$$\chi^2 = \sum_{i=1}^{N} \frac{(d_i - D_i(P_0, \ldots, P_M))^2}{\sigma_i^2} \qquad \text{Eq. (14)}$$

The quantity $x^2$ is a function of difference between two sets of quantities, d and D. The quantity $x^2$ is the sum of squares of the point-to-point differences between two sets of quantities, d and D. Each term in the summation is the squared difference between a value for d and a value for D, and where this difference is weighted by the square of the standard deviation σi.

To obtain correct parameter estimates for σi, only the relative noise values are important. For example, if all the terms have the same noise variance, then setting σi=1 for all terms (unweighted least-squares) will still yield the correct values for the parameters.

Least-squares fitting is then implemented by finding those parameters P that minimize the quantity $x^2$. Those values of P that minimize $x^2$ describe the model of D that best fits the data in a least-squares sense.

In order for least-squares fitting to be implement, an algorithm must be used to find the parameters $P_1, \ldots, PM$ that minimize $x^2$. As in any minimization procedure, the final values for $P_1, \ldots, PM$ will not depend on the details of the algorithm adopted to perform the minimization, as long as the minimum in $x^2$ is actually found.

In general, such minimization procedures require that initial parameters values be found and that an initial value for $x^2$ be computed. These parameters are then iteratively adjusted until the minimum of $x^2$ is found.

In the formulations of $x^2$ to be discussed below, the determination of initial parameters values can be accomplished by a variety of standard methods. Such methods include the manual estimation of values that are known to approximate the expected final parameter values; the adoption of typical values of parameters; or the implementation of a separate algorithm that determines initial parameters values from a subset of the data to be analyzed.

In the formulations of $x^2$ to be discussed below, the subsequent iterative adjustment of the parameters can be accomplished by a variety of standard methods. Methods that find the minimum of a function of N-variables include Newton-Raphson, Levenberg-Marquadt, simplex, gradient search, and brute force search. Such iterative adjustment procedures are described in the *Numerical Recipes in C, the Art of Scientific Computing, Second Edition,* (1992) W. H. Press, S. A. Teukolsky, W. T. Vetterling, B. P., Flannery, Univ. of Cambridge, pages 394–455, which is incorporated herein by reference.

In the prior art, the least-squares fitting procedure for RI-LS data is expressed as follows:

$$\chi^2 = \sum_{i=1}^{N} \left( \log\left(\frac{R_i}{c_i} \frac{1}{K^*}\right) - F_i(P_0, \ldots, P_M) \right)^2 \quad \text{Eq. (15)}$$

The above expression for $x^2$, being a least-squares minimization appears at first glance to be based on the theory of optimum estimation. However, it is not. In the prior art, the data model is correct, because the polynomial $$F_i = \sum_{j=0}^{M} P_j i^j$$

is generally an adequate representation of the molecular calibration curve. But the noise model is not correct.

The measurement error in $$\log\left(\frac{R_i}{c_i} \frac{1}{K^*}\right)$$

is non-Gaussian and is asymmetrical about zero. Also, there are no weighting factors, although the noise variance of each term is different.

In the method of the prior art, unweighted least-squares has the effect of increasing the influence of terms that contain excess noise and reducing the influence of terms that have good signal-to-noise in the estimation of parameters.

All implementations of least-squares model fitting must compare two sets of quantities. In Equation 14 the quantities that are compared are the data points d and the models of the data points D. In RI-LS detection, there are three sets of slice-dependent quantities to compare. These are the Rayleigh ratios Ri measured by the LS detector, the concentrations ci measured by the RI detector, and a model $$F_i = \sum_{j=0}^{M} P_j i^j$$

for the molecular weight of the slice versus elution volume.

Two successive improvements in the formulation of a least-squares minimization will now be described. The second formulation of least-squares minimization conforms to optimum estimation theory. All formulations use the same measured data values and the same parameterized model of the data, as in the prior art, but compare different quantities in performing the least-squares fit. Comparing different quantities effects a change in the noise model.

The first improvement removes the logarithms by exponentiating both terms in Equation 15. The least-squares comparison is then modified to become, $$\chi^2 = \sum_{i=1}^{N} \left( \frac{R_i}{c_i} \frac{1}{K^*} - 10^{F_i(P_0, \ldots, P_M)} \right)^2 \quad \text{Eq. (17)}$$

This rearrangement removes the bias due to logarithm and allows negative values of $R_i$ to be included. However, because $c_i$ is in the denominator, small values of $c_i$ in the peak tails will cause large fluctuations in this ratio.

The second improvement multiplies both terms by $c_i$ to arrive at new quantities to compare:

$$\chi^2 = \sum_{i=1}^{N} (R_i - c_i K^* 10^{F_i(P_0, \ldots, P_M)})^2 \quad \text{Eq. (18)}$$

This rearrangement allows the values for $c_I$ to be small.

The product of the concentration $c_i$, the optical constant $K^*$ and the polynomial model F, are compared to the Raleigh ratio Ri. Because the errors in Ri and ci are assumed to have zero mean and distributed as Gaussian, the error in each term on the right hand side of Eq. 18, will also be zero mean and distributed as a Gaussian.

In the formulation of Equation 18, all the profile data in the fit can be included, including points for which the measured values for Ri are consistent with zero and in fact have negative values due to noise. This solves the problem of using data in the tails of the distribution. The above expression thus can be used to fit for data throughout the peak region, including the tails.

Being able to fit values for Ri that are near zero represents a major advantage in the fitting of RI-LS data. The inclusion of such data near zero adds information that helps constrain the model fit. The inclusion of negative going fluctuations actually provides useful information to the fit that was not used in the method of the prior art.

The model $F_i$ in Eq. (18) is expressed as a polynomial expansion. However, the invention can incorporate any smooth, parameterized model curve in place of this polynomial expansion.

Equation 18 corresponds to unweighted least-squares. Generally, in the RI-LS system, the noise in the RI measurement is less than that of the LS measurement in the sense that the signal to noise ratio (SNR) of the peak apex in the RI profile is higher than that in the apex of the LS profile. If it is assumed that only the LS measurement is noisy and the RI measurement has essentially negligible noise, then unweighted least-squares yields the optimum, maximum likelihood estimate of the parameters P.

Figure 10:
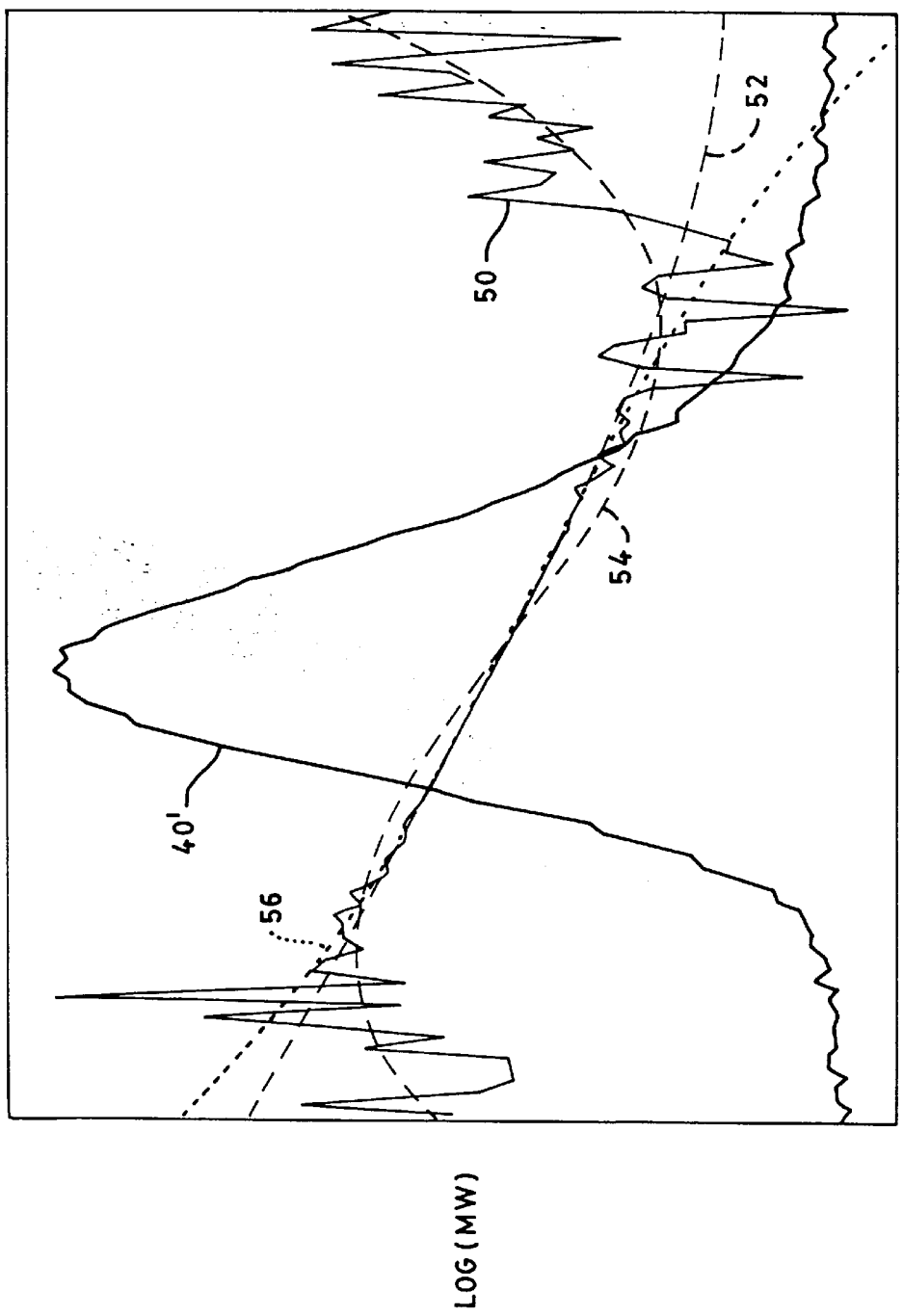
FIG. 10 illustrates the molecular weight calibration obtained from the illustrative embodiment as compared with a prior art method.

FIG. 10 plots $$\log\left(\frac{R_i}{c_i} \frac{1}{K^*}\right)$$

versus each slice number for a simulated separation as curve 50. Superimposed on the slice data is the model $$F_i = \sum_{j=0}^{M} P_j i^j$$

computed two different ways. One is by minimizing $x^2$ in the least-squares formulation of Equation 18, giving curve 52. The other is by minimizing $x^2$ in the least-squares formulation of Equation 15, giving curve 54. Curve 56 is the true log M calibration curve that corresponds to the central portion of curve 56 plotted in FIG. 5 and is overlaid here for comparison. The curve fit produced by the illustrative method is insensitive to the noise in the distribution's tail. The curve fit produced by the method of the prior art is dominated by the noise in the distribution's tail.

The measured quantities $c_i$ do contain noise. As noted, the least-square formulation can be generalized to include that as follows.

$$\chi^2 = \sum_{i=1}^{N} \frac{(R_i - c_i K^* 10^{F_i(P_0, \ldots, P_M)})^2}{\sigma_i^2} \qquad \text{Eq. (19)}$$

Here ηi can take into account the variance from both terms as follows:

$$\sigma_i^2 = \delta_i^2 + \gamma_i^2 (K^* 10^{F_i(P_0, \ldots, P_M)})^2 \qquad \text{Eq. (20)}$$

where $\delta i$ and $\gamma i$ are the standard deviations of the errors associated with the LS and RI detectors. The term in the bracket adjusts the relative contributions of these noise sources so they match the variance of the numerator. Here, the value for $\sigma i$ reflects the combined error in the LS and RI detectors. This formulation is exactly the one that gives the optimum estimate of the parameters P0, . . . ,PM, and conforms to the theory of maximum likelihood.

Even if ci contains significant noise, unweighted least-squares, Equation 18 can still be used. If unweighted least squares are used, all the data in the fit can still be included. The estimation of the parameter values will still be unbiased. The omission of a weighting function will result in somewhat increased sensitivity to the presence of detector noise in the profiles.

An additional rearrangement of the quantities in Eq. (18) can be performed so the least-squares formulation compares $(R_i/K^* 10^{F_i(P_0, \ldots, P_M)} - c_i)$. When the noise in the RI measurement is greater than the noise in the LS measurement, this rearrangement gives an optimum estimate of parameters P, using unweighted least-squares.

The next consideration is detection by a refractive index detector and a viscometer (RI-V). The goal of RI-V detection is to determine a sample's MWD and its IVL. These determinations both make use of the assumption of universal calibration.

To determine the sample's MWD, we must first determine the sample's molecular weight calibration curve, log Mi which is log molecular weight versus slice number or elution volume. To determine the IVL of a sample, log [η]i versus log Mi we must first determine log [η]i, log intrinsic viscosity versus elution volume. Combining log [η]i with log Mi gives us the sample's intrinsic viscosity law.

The viscometer determines the sample's specific viscosity, and the RI detector determines the sample's concentration at each slice. The intrinsic viscosity of a slice is the ratio of its specific viscosity to its concentration. The intrinsic viscosity is computed for each slice in a broad sample distribution as follows:

$$[\eta_i] = \eta_{sp,i}/c_i, \qquad \text{Eq.(21)}$$

where the subscript i refers to the ith data slice, and where [η]i is the intrinsic viscosity of slice i, ηsp,i is the specific viscosity, and ci is the concentration of the slice.

In a gel permeation chromatography (GPC) separation, the separation is effected by a size-dependent, not mass-dependent, interaction between the polymer chain and the chromatographic bed. The assumption of Universal Calibration introduced by Benoit [Z. Grubistic, R. Rempp, and H. Benoit, *J. Polym. Sci.*, Part B, 5, 753 (1967), which is incorporated herein by reference] is that the elution volume of a chain depends only on that chain's hydrodynamic volume. The hydrodynamic volume is defined to be the product of the molecular weight of a species times its intrinsic viscosity. Expressed in terms of slice quantities, this relation is:

$$H_i = M_i[\eta_i] \qquad \text{Eq.(22)}$$

The physical significance of this definition can be appreciated by substituting the definition of intrinsic viscosity to obtain:

$$H \equiv M[\eta] = M\frac{\eta_{sp}}{c} = \frac{\eta_{sp}}{\rho} \qquad \text{Eq. (23)}$$

where $\rho$ is the number density of the molecular species. Thus, hydrodynamic volume measures the viscosity per chain, in contrast to intrinsic viscosity, which measures viscosity per unit concentration.

The hydrodynamic volume for each slice is obtained by the use of narrow polymer standards of known molecular weight. RI-V detection determines the hydrodynamic volume for each standard. The standard's hydrodynamic volumes versus elution volumes can be plotted, and polynomial curves are fitted to this data to determine the hydrodynamic volume calibration curve. This curve gives the hydrodynamic volume of the column for each slice or elution volume spanned by the narrow standards. This curve is referred to either as the universal calibration of the column set, or as the hydrodynamic volume calibration curve.

The assumption of universal calibration leads to a method of calculating the absolute molecular weight distribution of a sample distribution using the responses obtained from the viscometer and RI detector. Given the hydrodynamic volume for each slice from the universal calibration curve, and the value of intrinsic viscosity obtained from each slice, we can simply compute the molecular weight of each slice from the definition $$M_i = \frac{H_i}{[\eta]_i} \qquad \text{Eq. (24)}$$

The straight forward application of Equations 21 and 24 to determine log [η]i and log Mi is only possible for that portion of the peak centered on the peaks apex. As in the case of light scattering, the noise in these quantities increases dramatically in the peak's tails, because the quantities log [η]i and log Mi both depends on the quantity log (ηsp, i/ci), which requires taking the logarithm of noise-affected detector responses.

In particular, the computation of molecular weight from the ratio of Equation 24 will usually not produce physically meaningful values in the tails of the distribution. That is, values for molecular weight computed from slice ratios will not monotonically decrease with increasing elution volume. Near the start and end-points of the profiles, they can be computed to be negative due to the influence of detector noise in the computation of [η]i for each slice.

However, both log Mi and log [η]i need to be measured over the whole peak region, including the peak tails. Again, as in the case of RI-LS, this is typically accomplished by fitting a smooth, parameterized model to log Mi and log [η]i as a function of a slice number or of elution volume. Since the quantities log Mi and log [η]i both tend to be nearly linear functions of elution volume, low-order polynomials as a function of elution are typically fit to these quantities.

How the data analysis of the prior art practice determines a model curve for the log of the intrinsic viscosities as measured for each slice versus elution volume will now be described. An expression of the following form is used:

$$\chi^2 = \sum_{i=1}^{N} \left( \log\left(\frac{\eta_{sp,i}}{c_i}\right) - \log[\eta]_i \right)^2 \quad \text{Eq. (25)}$$

where log $[\eta]i$ is a model curve describing the intrinsic viscosity as a function of slice i, and the M parameters P0, ..., PM such that $$\log[\eta_i] = \log[\eta(i; P_0, \ldots, P_M)] \quad \text{Eq. (26)}$$

The parameters P0, ..., PM are adjusted to minimize the value for $x^2$. Typically the form for log $[\eta]i = \log[\eta(i; P_0, \ldots, PM)]$ is a low order polynomial, such that $$\log[\eta(i; P_0, \ldots, P_M)] = \sum_{j=0}^{M} P_j i^j. \quad \text{Eq. (27)}$$

However, the invention can incorporate any smooth, parameterized model curve in place of this polynomial expansion.

Each term in the summation is the comparison between the log of the slice values and the intrinsic viscosity obtained from the model curve. This minimization obtains the estimates of the parameters describing the intrinsic viscosity versus slice number or elution volume.

In fitting this model curve, the same issues are faced as were dealt with in the RI-LS analysis. Again a low-order polynomial is fitted to the logarithm of the ratio of noise-affected detector responses. The noise in log ($\eta$sp,/ci) increases dramatically in the tails, and the logarithm of negative quantities is not defined. Because of the influence of detector noise in the tails, this method can only be applied to the heart of the peak. It is up to the user to decide the demarcation between the region to which the model is fit. In the prior art the intrinsic viscosity law in the peak tails is obtained by extrapolation from this model.

In the embodiment for finding the intrinsic viscosity versus slice number, the present invention reformulates the least-squares minimization by fitting a model of specific viscosity as a function of slice number or elution value to the measured values of specific viscosity for each slice. Thus, the x2 quantity to be minimized is:

$$\chi^2 = \sum_{i=1}^{N} (\eta_{sp,i} - 10^{\log[\eta]_i} c_i)^2 \quad \text{Eq. (28)}$$

Again the model for the IV curve is of the form of Equation 26. This expression performs a least-square minimization by comparing $\eta$sp,i to the product $[\eta]ici$. Specifically, this expression compares the measured specific viscosity of each slice to the product of the measured concentrations in each slice with the model, or fit-type, for the intrinsic viscosity law, for each slice.

In arriving at this expression, the exact same logic is used in reformulating the least-squares expression as was done for light scattering. The logs are exponentiated, and each term is multiplied by ci.

If the noise in ci is minimal, the unweighted expression for in equation (28) provides an optimum estimate for parameters Pi. If the measured slice values ci contain significant noise, a preferred expression is the following, $$\chi^2 = \sum_{i=1}^{N} \frac{(\eta_{sp,i} - 10^{\log[\eta]_i} c_i)^2}{\sigma_i^2} \quad \text{Eq. (29)}$$

which also conforms to the theory of maximum likelihood.

The advantages of these expressions are the same as in the case of RI-LS. The noise in the quantity $\eta_{sp,i} - [\eta_i]c_i$ in the numerator is nearly constant over the whole peak profile. In contrast, the noise in the quantity $$\log\left(\frac{\eta_{sp,i}}{c_i}\right) - \log[\eta]_i$$

is large in the peak tails. Again, this new method can determine the intrinsic viscosity of a distribution throughout the peak-in the heart of the peak and in the peak tails.

Once the model for log $[\eta]i$ is determined, the molecular weight for each slice throughout the peak can be determined from Equation 24. For each slice, Equation 24 is used to express Mi as the ratio of hydrodynamic volume, as obtained from the universal calibration curve, to the intrinsic viscosity, as obtained from the model fit of the present invention, via Equations 28 or 29. Since both Hi and $[\eta]i$ of Equation 24 are derived from smooth models, the resulting values for Mi will also not be significantly affected by noise in the detector's responses.

The present invention allows for an alternate determination of Mi from the analysis of data obtained by the RI-V system. This embodiment, again, employs a least-squares minimization that fits a model of specific viscosity as a function of slice number or elution volume to the measured values of specific viscosity for each slice. But now the model of specific viscosity depends on the slice values ci the hydrodynamic volume Hi and a model for the log molecular weight for each slice.

The quantity $x^2$ to be minimized is $$\chi^2 = \sum_{i=1}^{N} \left( \eta_{sp,i} - \frac{H_i}{10^{\log M_i}} c_i \right)^2, \quad \text{Eq. (30)}$$

where, again, log $M_I$ is described by a smooth parameterized model, which is typically a low order polynomial, as follows:

$$\log M_i = \log M(i; P_0, \ldots, P_M) = \sum_{j=0}^{M} P_j i^j \quad \text{Eq. (31)}$$

Again, the advantages of Equation 30 are the same as in the case of RI-LS. Again, as weighting function, if appropriate can be incorporated into this formulation, and these formulations are consistent with the theory of optimum estimation.

Once a model for the molecular weight versus slice number is obtained, the sample's MWD can be found. Once a model for the molecular weight versus slice number is obtained, and a model for intrinsic viscosity versus slice number is found, the intrinsic viscosity law, log $[\eta]i$, versus log Mi is known.

Physically motivated models for intrinsic viscosity can then be fit to the model values for log $[\eta]i$ versus log Mi. Examples of such models are the Mark-Houwink and Zimm-Stockmeyer laws, Equations 8 and 9. The advantage of fitting such laws to the models values for log $[\eta]i$ versus log $Mi$ is that the parameters describing those models usefully characterize the polymer sample under investigation. For example, the Mark-Houwink model can be fit to a portion of the low-molecular weight region of a branched polymer to obtain $K$ and $\alpha$ for that region. The ZS model can be fit to the slice values for log $[\eta]i$ versus log $Mi$ over the complete peak of a branched polymer to obtain $K$ and $a$ for the low molecular-weight region, as well as the branching probability $\alpha$ and the shape factor $\epsilon$ for the polymer sample.

Even though application of the present invention produces improve values for log $[\eta]i$ versus log $Mi$ as compared to methods of the prior art, the determination of the physical parameters of intrinsic viscosity laws can suffer from a remaining drawback in these methods. The values for parameters that describe the intrinsic viscosity law depend upon the form of the models assumed to represent both log $[\eta]i$ and log $Mi$ versus slice elution volume. If these polynomial (or other assumed) models are inaccurate in describing the true dependencies of log $[\eta]i$ and log $Mi$ versus elution volume, then the accuracy of parameters describing the intrinsic viscosity laws will suffer a corresponding inaccuracy.

This source of inaccuracy is not due to detector noise. Rather it arises from the errors in the form of model curves used to describe log $[\eta]i$ and log $Mi$ versus elution volume. It is worth noting that these models must account for the molecular weight calibration curve for the column, as well as the intrinsic character of the polymer.

The next embodiment of the present invention is directed towards determining the parameters of the intrinsic viscosity law by solving two relationships simultaneously over the whole of the data analysis region. In this method, the IV law is determined directly from the slice data and does not require the assumption of additional ancillary models.

The two relationships to be solved are:
1. The least squares comparison of the measured specific viscosity to a prediction of the specific viscosity, which is the product of the intrinsic viscosity law model and a slice measurement of concentration. The least squares comparison is:

$$\chi^2 = \sum_{i=1}^{N} (\eta_{sp,i} - [\eta]_i c_i)^2 \qquad \text{Eq. (32)}$$

where $\chi^2$ is the sum of the squares of differences computed for each slice. In this expression, the intrinsic viscosity law is a function of log molecular weight, and the form of the intrinsic viscosity is $$\log[\eta_i] = \log[\eta(\log M_i; P_1, \ldots, P_M) \qquad \text{Eq. (33)}$$

Because the MW calibration is not yet known, the minimum of this expression cannot be found without additional information. This additional information is provided by the second relationship to be solved, which is:
2. The fundamental relationship between hydrodynamic volume, intrinsic viscosity and molecular weight, for each slice i:

$$H_i = M_i[\eta_i] \qquad \text{Eq. (34)}$$

Again, the intrinsic viscosity law is described by Equation 33.

Equation 34 is used to eliminate the dependence of $Mi$ in Equation 33, the sample's IVL. Thus, given an explicit form of an IVL, an important part of the present invention includes re-expressing the IVL so that $[\eta]i$ depends only on the parameters $P1, \ldots, PM$ and the hydrodynamic volume $H_i$.

This algebraic substitution will be explicitly demonstrated in the case of the linear IVL below. In the case of more complex IVLs, such as are described in Equations 9 and 10, simple algebraic substitution may not suffice to determine $[\eta]i$ as a function of $H_i$ in closed form. Given Equation 33, values for $P1, \ldots, PM$ and $H_i$, Equation 34 can be solved, using numerical methods, to give the value for $[\eta]i$, These numerical methods (the solution of equations through root finding) are described in *Numerical Recipes in C, The Art of Scientific Computing, Second Edition,* (1992) W. H. Press, S. A. Teukolsky, W. T. Vetterling, B. P. Flannery, Univ. of Cambridge, pages 347–393 which is incorporated herein by reference.

Thus, Equation 32 now depends explicitly only on the measured quantities $\eta sp,i$, $c_i$, $H_i$ and the parameters $P1, \ldots, PM$. No explicit reference is made to log $M$ in this final formation of Equation 32. Also, in contrast to the prior art, there is no reference to elution volume as an independent variable. Thus, the parameters of the IVL are determined by a single fit to the measured detector responses.

After minimization, a fitted value for $[\eta]i$ for each slice has been obtained. From this value and the known value for Hi, Mi is determined from direct computation from the fundamental relationship $H_i \equiv M_i[\eta_i]$. The MWD of the sample is thereby obtained. Again, no additional fit is required.

Figure 11:
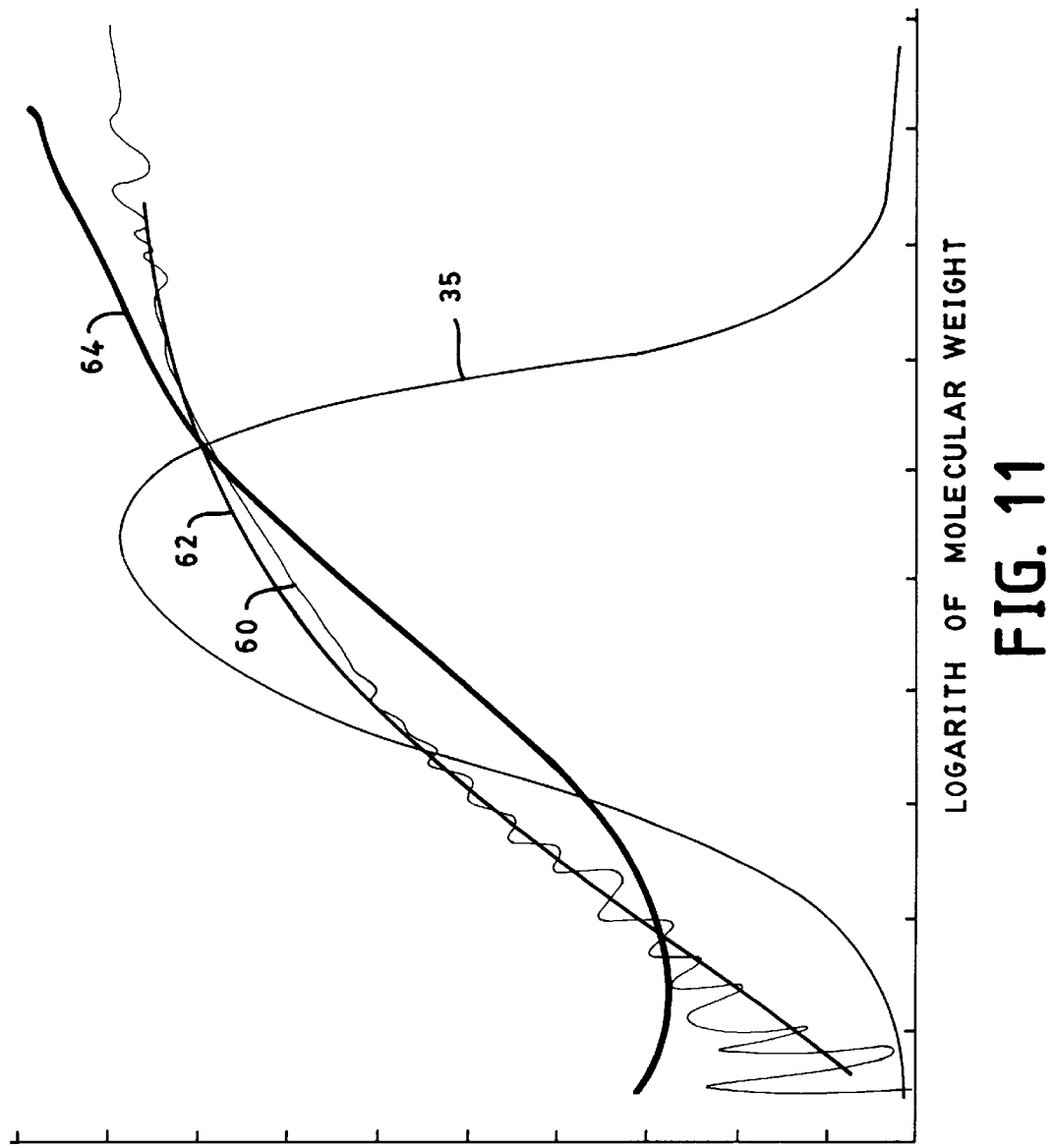
FIG. 11 displays the sample's IV law determined from RI-V detection according to the illustrative embodiment as compared to a prior art method.

FIG. 11 plots the IV law as determined by the prior art method which relies on extrapolation, and the IV law as determined by the illustrative method. Four curves are superposed: the IV determined from the slices 60, the IV law determined from the illustrative method of the present invention 62, the IV law determined by the method of the prior art 64, and the sample's MWD for reference 35, FIG. 3.

As in the case of light-scattering, the least-squares problem is now formulated to avoid taking ratios or logarithms of ratios of noisy data. The noise in each term is of the same magnitude so the use of unweighted least-squares is appropriate. The fit can be performed to all the baseline-corrected data in the peak region. The measured values $\eta sp,i$ and ci can be near zero and contain noise that causes these responses to fluctuate about zero.

In the present invention for the formulation of $\chi^2$, the inclusion of measurements consistent with zero response actually improves the constraints on the parameters describing the IVLs, such as $K$ and $\alpha$. Therefore the present invention is considerably less sensitive to measurement errors, especially in the tails of the peaks.

Further, the advantage of fitting two equations simultaneously means that the IV law and molecular weight calibration are estimated from a single fit to all the slice data. Performing multiple fits and extrapolations is no longer necessary. In the prior art, the additional fit is a potential source of systematic error, as special, column-dependent fit-types might have to be assumed.

In the case where the IV law is linear, Equation 8, $\log[\eta_i] = \log K + \alpha \log M$, is re-expressed as $[\eta_i] = KM^\alpha$. so the relationship between hydrodynamic volume and molecular weight is $H = KM^{\alpha+1}$.

We can therefore eliminate $M_i$ and express the IVL as $$[\eta]_i = K^{\frac{1}{1+\alpha}} H_i^{\frac{\alpha}{1+\alpha}}. \qquad \text{Eq. (35)}$$

The expression to be minimized is then:

$$\chi^2 = \sum_{i=1}^{N} \left( \eta_{sp,i} - K^{\alpha+1} H_i^{\frac{\alpha}{1+\alpha}} c_i \right)^2 \qquad \text{Eq. (36)}$$

In this final form, $x^2$ is expressed only in terms of the measured slice values, $\eta sp,i$, Hi, and ci, and the parameters K and $\alpha$. No explicit reference to elution volume is made.

Given that the values of K and $\alpha$ that minimize $x^2$ are found by some suitable minimization algorithm, the molecular weight of each slice is obtained from the relationship $M_i = (H_i/K)^{1/(1+\alpha)}$, and the model values for $[\eta]_i$ for slice i are obtained from Eq. (35).

In the illustrative embodiment, the present invention is implemented using the formulation described in Equations 8, 9 and 10, which define three fit-types for the logarithmic intrinsic viscosity law. These are a linear function of log molecular weight, a Zimm-Stockmeyer law describing long-chain branching, and a higher order polynomial function.

Figure 12:
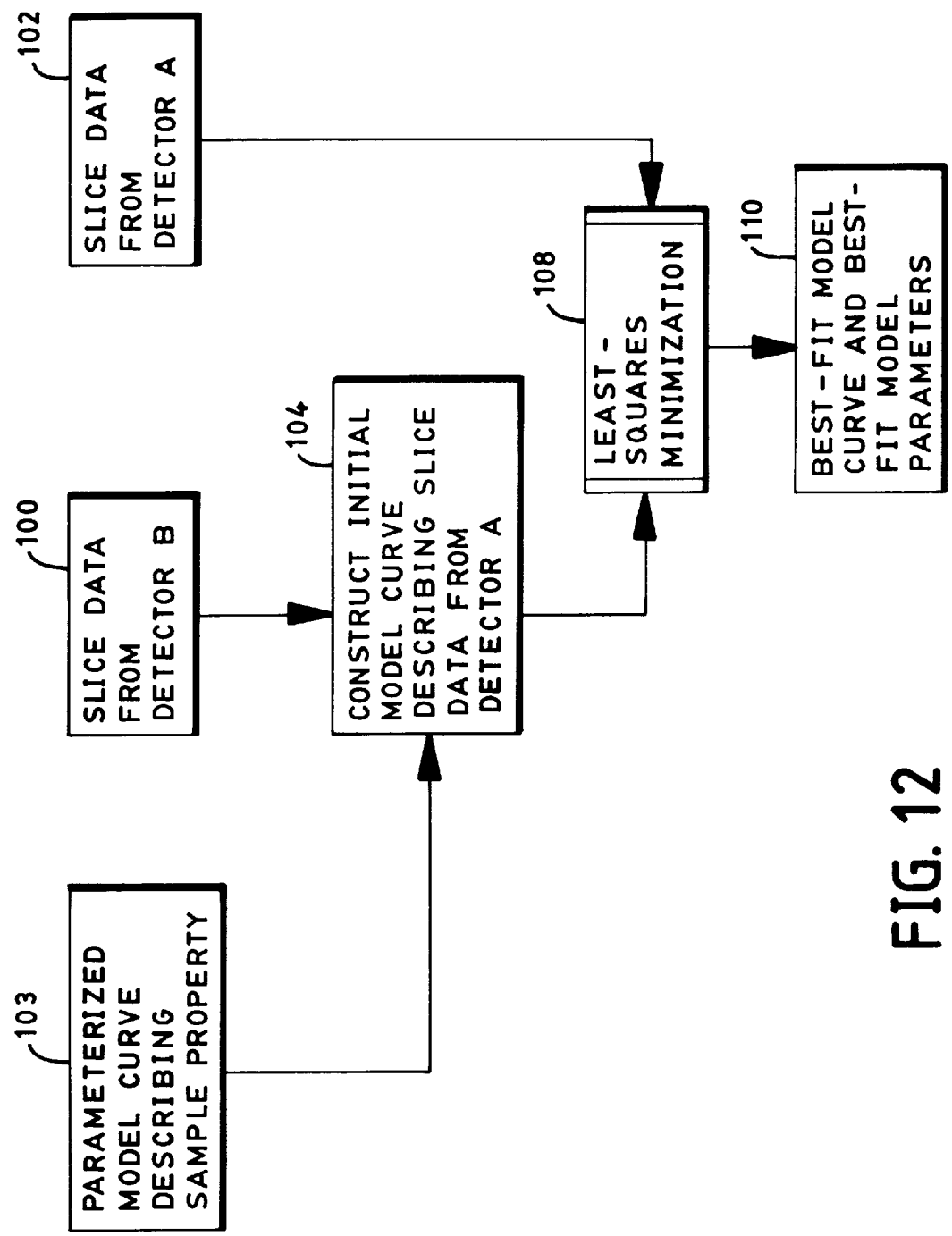
FIG. 12 is an overview of the steps performed according to one embodiment of the present invention.

FIG. 12 illustrates the steps performed by an illustrative embodiment of the present invention as described in detail hereinbefore. Data 100 obtained from a first detector (for example, slice data from a concentration detector) is combined with a parameterized model curve describing the sample property 103 to construct a model curve, step 104. Data 102 is obtained from a second detector (for example, slice data from a molecular weight sensitive detector). A least-squares minimization algorithm is performed, step 108. Details of the least-squares minimization algorithm will be described below. The result is a best fit model curve and parameters, step 110.

Figure 13:
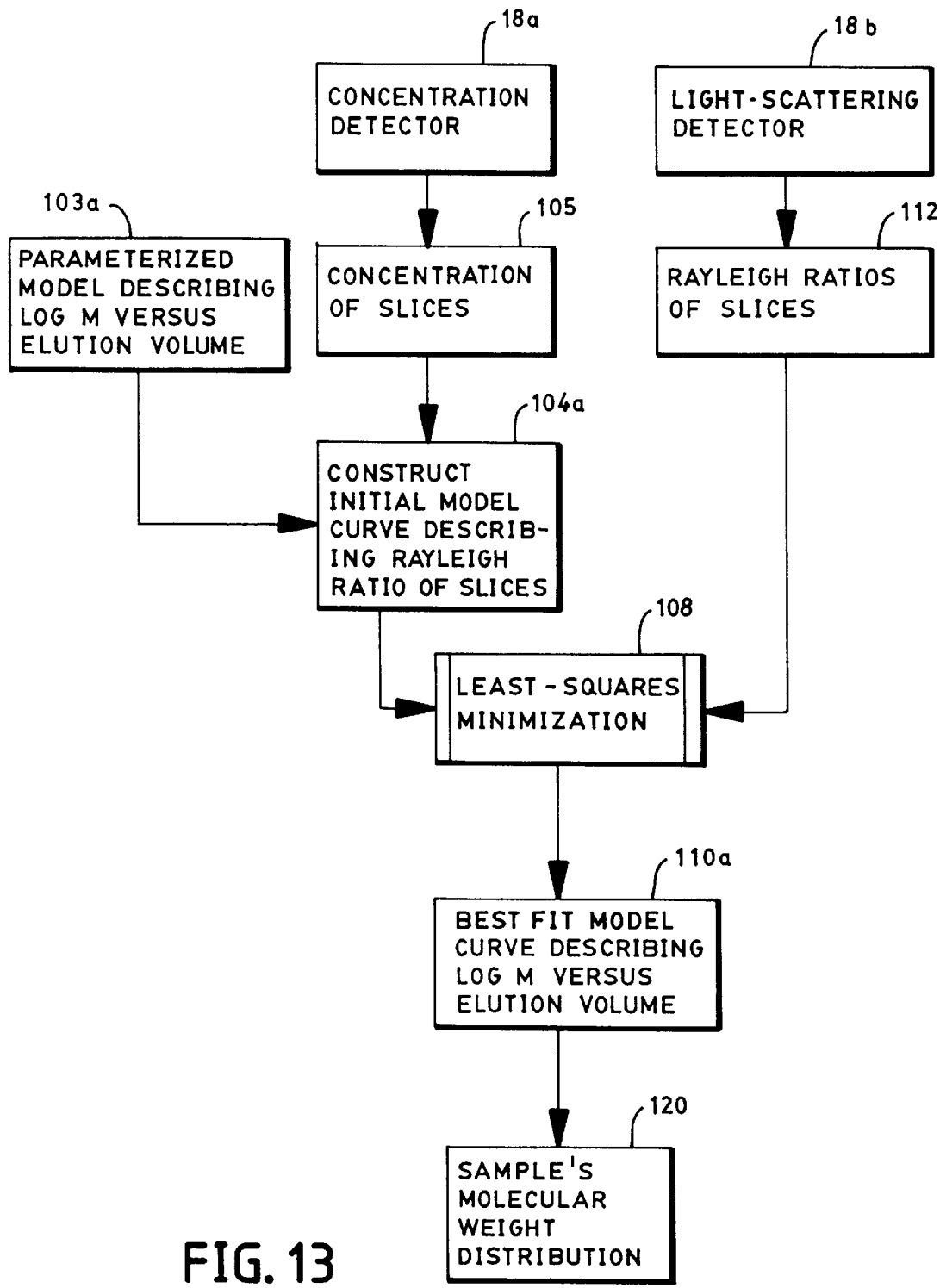
FIG. 13 is an overview of the steps performed for estimating a sample's molecular weight distribution (MWD) from RI-LS detection in accordance with the embodiment of FIG. 12.

FIG. 13 illustrates the steps for an embodiment for estimating a sample's molecular weight distribution (MWD) from RI-LS detection as described in detail hereinbefore. Data is obtained from a concentration sensitive detector (such as an RI detector) 18a. The data is processed obtaining the concentration of slices, step 105. A parameterized model describing log M versus elution volume (Eq. 13) 103a is used with the concentration slices 105 to construct a model curve describing Rayleigh Ratio of the slices by $$c_i K^* 10^{F_i(P_0, \ldots, P_M)} \qquad \text{Eq.(37)}$$

in step 104a. Second data from a molecular weight sensitive detector (such as an LS detector) 18b is processed into slices, and the Rayleigh Ratio is determined for each slice, step 112. A least-squares minimization algorithm is performed using Eq. (18) or Eq. (19), step 108, resulting in a best fit model curve describing log M versus elution volume, as shown by curve 52 in FIG. 10. The sample's molecular weight distribution is then produced, step 120 FIG. 13.

Figure 14:
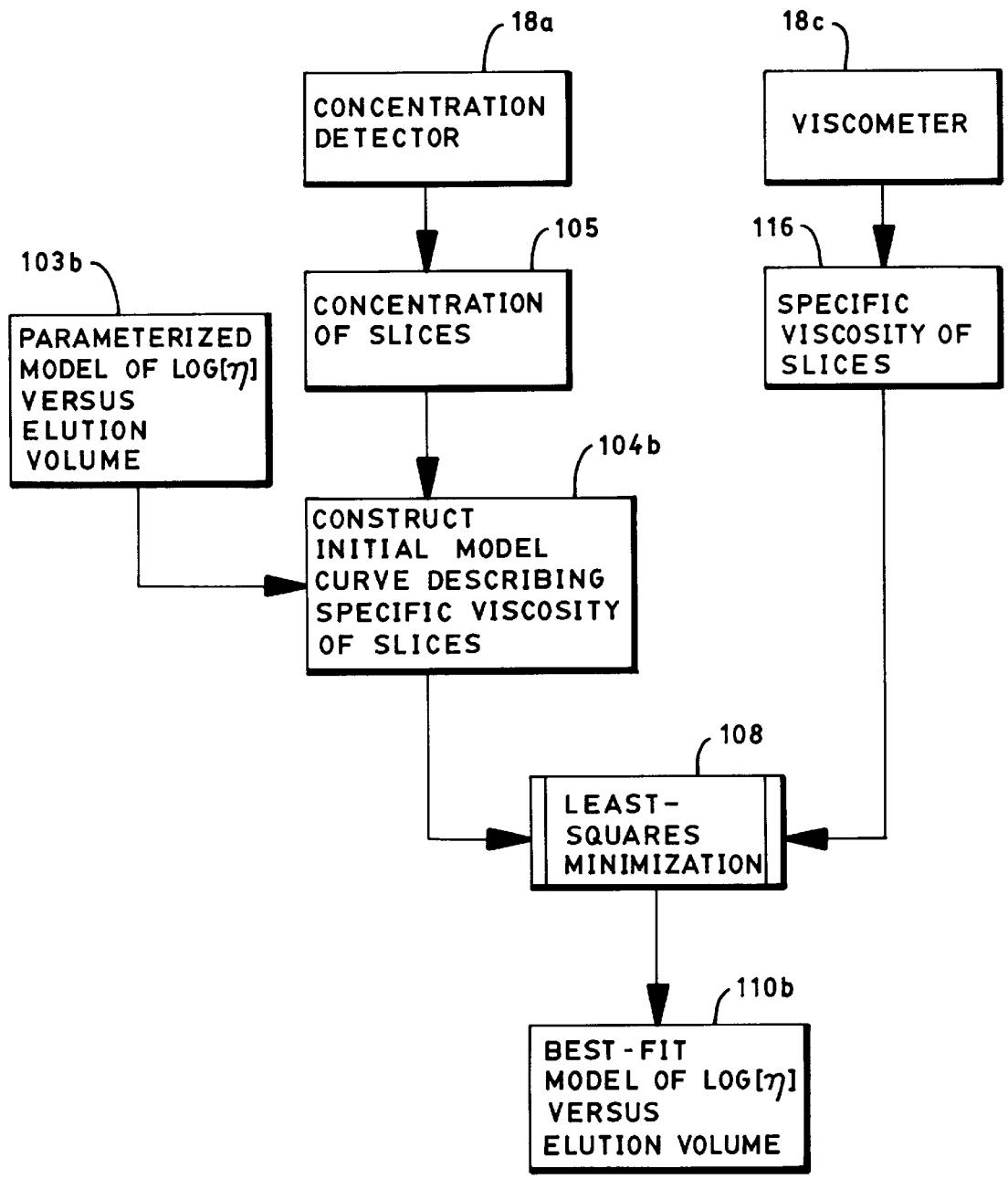
FIG. 14 is an overview of the steps performed for estimating a sample's intrinsic viscosity versus elution volume from RI-V detection in accordance with the embodiment of FIG. 12.

FIG. 14 illustrates the steps for an embodiment for estimating a sample's intrinsic viscosity from RI-V detection, as described in detail hereinbefore. Data is obtained from a concentration sensitive detector (such as an RI detector) 18a. The data is processed as a concentration of slices, step 105. A parameterized model describing log $[\eta_i]$ versus elution volume (Eq. 27) 103b is used with the concentration slices 105 to construct a model curve describing specific viscosity of the slices, by $$c_i 10^{\log[\eta_i]} \qquad \text{Eq. (38)}$$

in step 104b. Second Data from a viscosity detector 18c is processed using the specific viscosity for slices, step 116. A least-squares minimization is performed, using Eq. (28) or Eq. (29) step 108. A best-fit model of log $[\eta_i]$ versus elution volume (Eq. (27)) is produced, step 110b.

Figure 15:
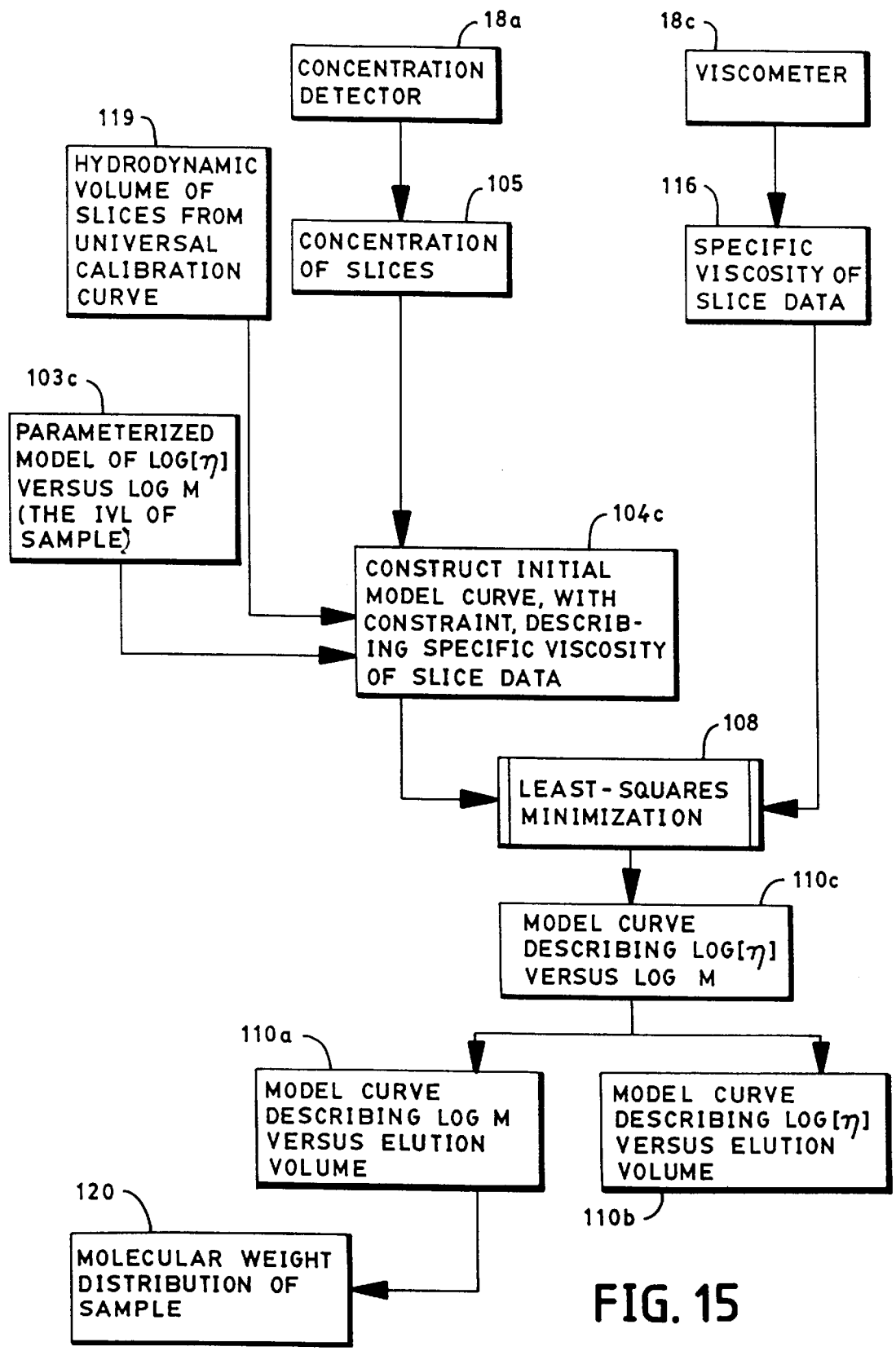
FIG. 15 is an overview of the steps performed according to another embodiment for estimating a sample's intrinsic viscosity law and molecular weight distribution from RI-V detection according to the present invention.

FIG. 15 illustrates the steps performed according to another embodiment for simultaneously estimating a sample's intrinsic viscosity and molecular weight distribution from RI-V detection according to the present invention, as described in detail hereinbefore. Data is obtained from a concentration sensitive detector (such as an RI detector) 18a. The data is processed as a concentration of slices, step 105. A parameterized model describing log $[\eta_i]$ versus log M (the IVL) 103c, Eq. (33), is used with concentration slices to construct an initial model curve, step 104c. Also used to construct the model curve is hydrodynamic volume of slices from the universal calibration curve, step 119. The initial model curve produced in step 104c includes constraints describing intrinsic viscosity of slice data (Eq. (34)).

Second Data from a viscosity detector 18c is processed obtaining the specific viscosity for slices, step 116. A least-squares minimization, step 108, is performed on the constructed initial model curve 104c and the specific viscosity of slice data 116 (Eq. 32). A model curve describing log $[\eta_i]$ versus log M is produced, step 110c, (Eq. 33). From this curve 110c, the model curve describing log M versus elution volume, is produced, step 110a, according to $$\log M_i = \log H_i - \log[\eta_i] \qquad \text{Eq. (39)}$$

and the sample's molecular weight distribution is then produced, step 120. Finally, also from the curve 110c the model curve of log $[\eta_i]$ versus elution volume is produced, step 110b.

Figure 16:
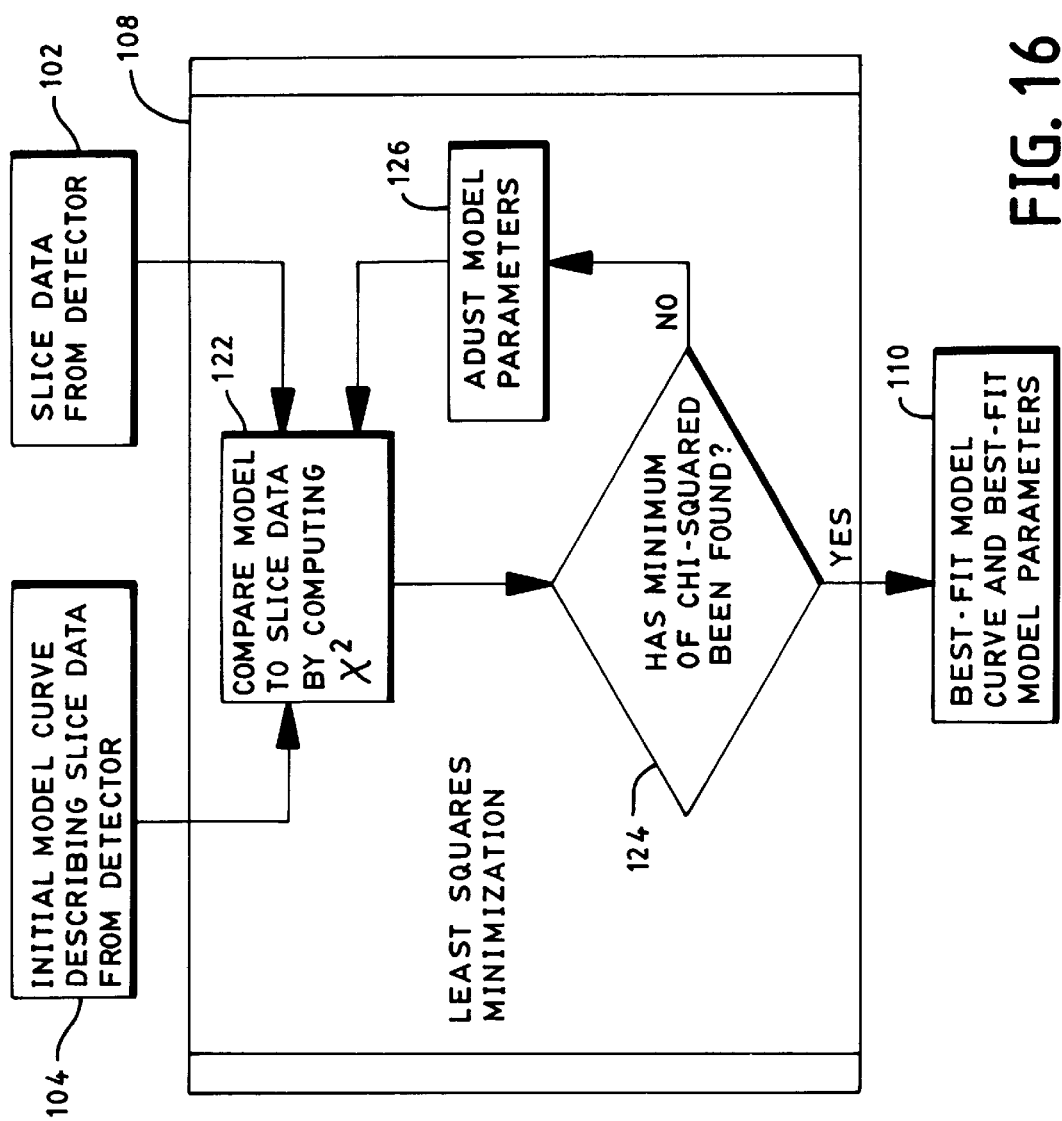
FIG. 16 is an overview of the least-squares fit step utilized by the embodiments shown in FIGS. 12–15.

FIG. 16 details the least-squares minimization step 108 of FIGS. 12–15. The initial model curve 104 (produced from slice data from a concentration detector 18a) is compared with slice data 102 from a detector 18b, by computing $x^2$ using the equations including Equations 18, 19, 28, 29, 30, 32 and 36. As previously described the model parameters are adjusted, step 126, and $x^2$ is again computed until $x^2$ has been minimized, step 124. At this point, the best fit model curve and best fit model parameter have been determined, step 110.

While specific examples of RI, V and LS detectors are described in the embodiments herein, it will be appreciated that other detectors, such as other models and/or from other manufacturers, can be implemented.

Although the invention has been shown and described with respect to exemplary embodiments thereof, various other changes, omissions and additions in the form and detail thereof may be made therein without departing from the spirit and scope of the invention.

What is claimed is:

1. On a computer system, a method of determining molecular weight distribution (MWD) of a sample processed using gel permeation chromatography apparatus, said method comprising:

obtaining first data from a first detector detecting said sample;

obtaining a parameterized model describing sample properties;

choosing initial values for parameters for said parameterized model;

constructing an initial curve from said first data, from said parameterized model, and from said initial values;

obtaining second data from a second detector detecting said sample;

determining a best fit curve and best fit parameter values from said initial curve, from said parameterized model, and from said second data to provide a molecular weight calibration for said chromatography apparatus; and obtaining a concentration profile of said sample using said chromatography apparatus, and using said molecular weight calibration and said concentration profile to determine said MWD.

2. The method of claim 1 wherein said first detector includes a concentration sensitive detector.

3. The method of claim 1 wherein said second detector includes a molecular weight sensitive detector.

4. The method of claim 1 wherein said second detector includes a Light Scattering (LS) detector.

5. On a computer system, a method of determining intrinsic viscosity versus elution volume of a sample processed by gel permeation chromatography, said method comprising:

obtaining first data from a first detector detecting said sample;

obtaining a parameterized model describing log intrinsic viscosity versus elution volume;

choosing initial values for parameters for said parameterized model;

constructing an initial curve of specific viscosity from first data, from said parameterized model, and from said initial values;

obtaining second data from a second detector detecting said sample; and determining a best fit curve of specific viscosity and best fit parameter values of said model of log intrinsic viscosity versus elution volume from said initial curve, from said parameterized model, and from said second data.

6. The method of claim 5 wherein said first detector includes a concentration sensitive detector.

7. The method of claim 5 wherein said second detector includes a molecular weight sensitive detector.

8. The method of claim 5 wherein said second detector includes a viscometer (V) detector.

9. On a computer system, a method of substantially simultaneously determining molecular weight distribution (MWD) and intrinsic viscosity (IVL) of a sample processed by gel permeation chromatography, said method comprising:

obtaining first data from a first detector detecting said sample;

obtaining a parameterized model describing log intrinsic viscosity versus log molecular weight;

choosing initial values for parameters for said parameterized model;

obtaining hydrodynamic volume of slices from a universal calibration curve;

constructing an initial curve of specific viscosity from said first data, from said parameterized model, from said initial values, and from said hydrodynamic volume of slices;

obtaining second data from a second detector detecting said sample;

determining a best fit curve of specific viscosity and best fit parameters values of said model of log intrinsic viscosity versus log molecular weight from said initial curve, from said parameterized model, and from said second data;

determining IVL from said parameterized model and said best fit parameter values;

obtaining molecular weight calibration from said IVL; and determining said MWD from said molecular weight calibration.

10. The method of claim 1 wherein said initial curve represents a Rayleigh ratio of said sample versus elution volume.

11. The method of claim 1 wherein said step of obtaining said parameterized model involves obtaining a model that describes molecular weight calibration as a function of elution volume.

12. The method of claim 1 wherein said step of determining said best fit curve and best fit parameter values involves performing a least squares minimization fit on said initial curve, said parameterized model, and said second data.

13. The method of claim 1 wherein said concentration profile is obtained using said first detector.

14. The method of claim 5 wherein said step of determining said best fit curve and best fit parameter values of said model of log intrinsic viscosity versus elution volume involves performing a least squares minimization fit on said initial curve, said parameterized model, and said second data.

15. The method of claim 9 wherein said step of determining said best fit curve of specific viscosity and best fit parameters values of said model of log intrinsic viscosity versus log molecular weight involves performing a least squares minimization fit on said initial curve, said parameterized model, and said second data.

16. The method of claim 9 wherein said first detector includes a concentration sensitive detector.

17. The method of claim 9 wherein said second detector includes a molecular weight sensitive detector.

18. The method of claim 9 wherein said second detector includes a viscometer (V) detector.

* * * * *